(12) United States Patent
Kim et al.

(10) Patent No.: US 11,279,756 B2
(45) Date of Patent: Mar. 22, 2022

(54) BINDING MOLECULE SPECIFIC FOR LRIG-1 PROTEIN AND USE THEREOF

(71) Applicant: GOOD T CELLS, INC., Seoul (KR)

(72) Inventors: Jung Ho Kim, Seoul (KR); Beom Seok Kim, Seoul (KR)

(73) Assignee: GOOD T CELLS, INC., Seoul (KR)

( * ) Notice: Subject to any disclaimer, the term of this patent is extended or adjusted under 35 U.S.C. 154(b) by 131 days.

(21) Appl. No.: 16/606,220

(22) PCT Filed: Apr. 18, 2018

(86) PCT No.: PCT/KR2018/004523
§ 371 (c)(1),
(2) Date: Oct. 17, 2019

(87) PCT Pub. No.: WO2018/194380
PCT Pub. Date: Oct. 25, 2018

(65) Prior Publication Data
US 2020/0131261 A1    Apr. 30, 2020

(30) Foreign Application Priority Data

Apr. 18, 2017  (KR) .......................  10-2017-0049854

(51) Int. Cl.
*C07K 16/18* (2006.01)
*C07K 14/47* (2006.01)
(Continued)

(52) U.S. Cl.
CPC .............. *C07K 16/28* (2013.01); *A61P 35/00* (2018.01); *A61P 37/06* (2018.01);
(Continued)

(58) Field of Classification Search
None
See application file for complete search history.

(56) References Cited

U.S. PATENT DOCUMENTS

| 2020/0048343 A1 | 2/2020 | Kim et al. |
| 2020/0131261 A1 | 4/2020 | Kim et al. |

FOREIGN PATENT DOCUMENTS

| KR | 10-2086656 B1 | 3/2020 |
| KR | 10-2086649 B1 | 4/2020 |

OTHER PUBLICATIONS

Shirani, A., Okuda, D.T. & Stüve, O. Therapeutic Advances and Future Prospects in Progressive Forms of Multiple Sclerosis. Neurotherapeutics 13, 58-69 (2016). (Year: 2016).*

(Continued)

*Primary Examiner* — Aurora M Fontainhas
(74) *Attorney, Agent, or Firm* — Marshall, Gerstein & Borun LLP

(57) ABSTRACT

The present invention relates to a binding molecule capable of specifically binding to Lrig-1 protein, which is located on the surface of a regulatory T cell. The binding molecule provided in the present invention can activate the function of regulatory T cells to effectively prevent, ameliorate, or treat diseases caused by excessive activation or expression of various immune cells and inflammatory cells, for example, immune-related diseases such as autoimmune disease, graft-versus-host disease, organ transplant rejection, asthma, atopy, acute or chronic inflammatory disease, etc. In addition, the binding molecule, preferably the antibody, specific for the Lrig-1 protein according to the present invention has advantages of more effectively targeting the Lrig-1 protein as compared with antibodies against Lrig-1 which are previously commercially available, and also possessing very good binding capacity thereto.

12 Claims, 12 Drawing Sheets

Specification includes a Sequence Listing.

(51) Int. Cl.
*C07K 16/28* (2006.01)
*A61P 35/00* (2006.01)
*A61P 37/06* (2006.01)
*A61K 39/00* (2006.01)

(52) U.S. Cl.
CPC .... *A61K 2039/505* (2013.01); *C07K 2317/21* (2013.01); *C07K 2317/52* (2013.01); *C07K 2317/565* (2013.01); *C07K 2317/76* (2013.01)

(56) References Cited

OTHER PUBLICATIONS

Kussie et al., A single engineered amino acid substitution changes antibody fine specificity. J Immunol. Jan. 1, 1994;152(1):146-52. (Year: 1994).*

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

French, How to make bispecific antibodies, Methods Mol. Med., 40:333-339 (2000).

GenBank: Accession No. AAA59000.1: Immunoglobulin Kappa Chain V-J-C, Partial [*Homo sapiens*], dated Jul. 26, 2016.

GenBank: Accession No. AAA02914.1: IgG [*Homo sapiens*], dated Apr. 27, 1993.

GenBank: Accession No. AAN86780.1, Immunoglobulin Heavy Chain, Pariial [Mus musculus], dated Jul. 24, 2016.

GenBank: Accession No. CAC20700.1, Immunoglobulin Light Chain Constant Region Kappa, Partial [Mus musculus], dated Jun. 11, 2015.

Jackson et al. In vitro antibody maturation. Improvement of a high affinity, neutralizing antibody against IL-1 beta, J Immunol., 154(7):3310-3359 (1995).

Nilsson et al., LRIG1 protein in human cells and tissues, Cell. Tiss. Res., 312:65-71 (2003).

Pearson, Using the FASTA program to search protein and DNA sequence databases, Meth. Mol. Biol., 24:307-331(1994).

Schier et al., Identification of functional and structural amino-acid residues by parsimonious mutagenesis, Gene., 169(2):147-155 (1995).

Suzuki et al.. Targeted disruption of LIG-1 gene results in psoriasiform epidermal hyperplasia, Febs. Lett., 521(1-3) 67-71 (2002).

Tanemura et al., LRIG-1 Provides a Novel Prognostic Predictor in Squamous Cell Carcinoma of the Skin Immunohistochemical Analysis for 38 Cases, Dermato. Surg., 31(4);423-430 (2005).

* cited by examiner

[FIG. 1]
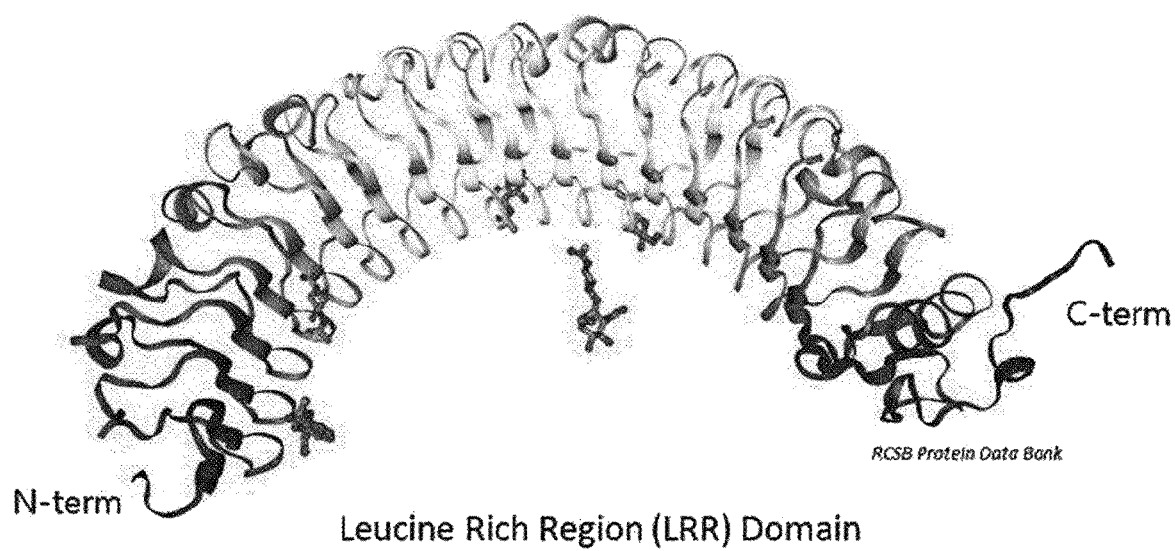
Leucine Rich Region (LRR) Domain
[FIG. 2]
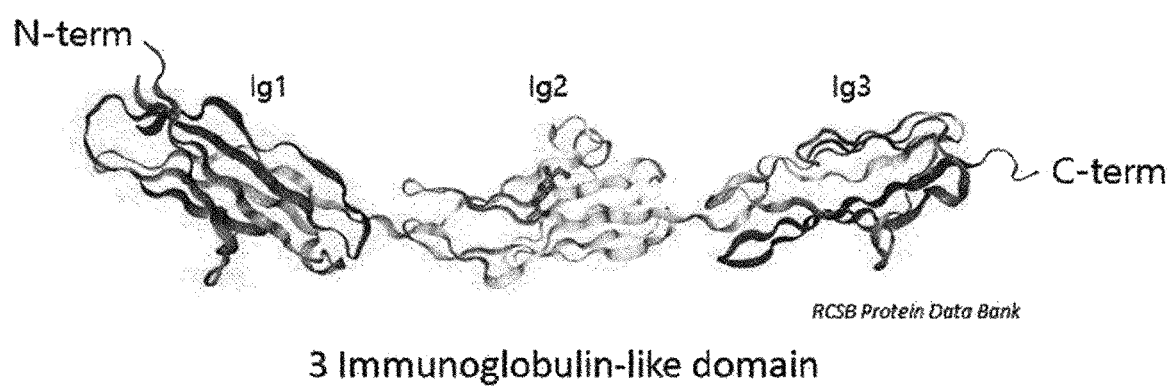
3 Immunoglobulin-like domain

| No. | Chain | Start | End | Peptide | Number of Residue | Score |
|---|---|---|---|---|---|---|
| 1 | A | 9 | 56 | GDSLDCGGRGLAALPGDLPSSTRGMLSYMLSEDPAGFEDLPALGE | 48 | 0.88 |
| 2 | A | 399 | 455 | SDSFLCDCCDLMVLPPWLGRMLDAFVTATCAHPESLKGDSFSVPRESFVCDDALKA | 57 | 0.853 |
| 3 | A | 60 | 66 | NIMELTA | 7 | 0.814 |
| 4 | A | 376 | 393 | NARSVCFDAFVKWNLK | 18 | 0.586 |
| 5 | A | 85 | 89 | NKPS | 5 | 0.561 |
| 6 | A | 232 | 237 | VEVISG | 6 | 0.541 |
| 7 | A | 256 | 261 | ARIHPK | 6 | 0.539 |
| 8 | A | 109 | 117 | KNTEVRNT | 9 | 0.52 |
| 9 | A | 183 | 196 | IRLEGLTFCGLNS | 14 | 0.52 |
| 10 | A | 207 | 220 | ISKLTDGAFVIGLSK | 14 | 0.514 |
| 11 | A | 158 | 170 | NRTDLPVRAPLL | 13 | 0.501 |
| 12 | A | 96 | 101 | KAYLSL | 6 | 0.5 |
| 13 | A | 531 | 555 | KKDNEVLTMADMEKFVMHAVMEYT | 25 | 0.82 |
| 14 | A | 517 | 527 | SAASSSSSRMT | 11 | 0.817 |
| 15 | A | 727 | 744 | FKGDPLSLTEPHHLTPD | 18 | 0.781 |
| 16 | A | 777 | 786 | QLSVLLEMLY | 10 | 0.772 |
| 17 | A | 494 | 501 | KFCMTCP | 8 | 0.732 |
| 18 | A | 697 | 711 | VPLEDRVVSVGETVA | 15 | 0.721 |
| 19 | A | 849 | 858 | HVMPDDIVFF | 10 | 0.69 |
| 20 | A | 579 | 590 | ITNHPGSSTYSHK | 12 | 0.678 |
| 21 | A | 748 | 760 | QLLVVCNVVAEDAGR | 15 | 0.656 |
| 22 | A | 563 | 570 | HLRDVTFG | 8 | 0.504 |

[FIG. 3]

| No. | Peptide | Number of Residue | Score |
|---|---|---|---|
| 1 | C1, P2, S3, R4, C5, T6, C7, S8, G9, D10, S11, L12, D13, C14, G15, G16, R17, G18, L19, A20, A21, L22, P23, G24, D25, L28, P27, S28, S29, T30, R31, S32, L33, K34, L35, S36, Y37, N38, K39, L40, S41, E42, I43, D44, P45, A46, G47, F48, E49, D50, L51, P52, N53, L54, G55, E56, L58, N60, N61, M62, E63, L64, A66, P68, S69, L70, G71, A72, A73, S74, S75, H76, V78, H84, N85, K86, B7, R88, S89, H98, A97, Y98, L99, S100, L101, P120, H121, G122, P123, P124 | 91 | 0.747 |
| 2 | N109, M110, I111, T112, E113, R115, M116, T117, N133, R134, I135, G136, T137, E138, L140, G141, A142, M153, R159, I160, T161, Q182, L183, P164, V185, R186, A167, K169, L170, P171, R182, I183, L186, E187, G188, L189, T190, Q192, Q193, L194, M195, S196, E207, S228, T211, D212, G213, A214, F215, W216, G217, L218, S219, K220, S229, L231, V232, E233, V234, N235, S236, G237, Y240, G241, L242, T243, A244, A258, R257, R260, K261, S264, F262, E264, C267, E284, E285, S298, L287, A268, L290, S291, A307, E308, E309, K312, R313, R315, S318, S325, G333, G334, S339, G340, L341, D342, I354, K355, K358, L365, E308, G367, E389, M378, A377, I379, R379, S380, V381, C362, F383, D384, A385, V387, K388, M389, K280, N391, L392, R383, S388, D400, S401, F402, L403, C404, D405, C408, Q407, L408, P412, P413, W414, L415, A18, Q417, R418, L420, Q421, C404, A422, F423, V424, T425, C428, A428, H429, K430, P431, E432, S433, L434, K435, G438, C437, S438, K439, S441, V442, P443, P444, E446, S446, F447, V448, C448, D450, D461, F452, L463, K454, A455 | 178 | 0.826 |
| 1 | M704, L795, Y786 | 3 | 0.877 |
| 2 | K494, P485, Q498, M487, I498, T493, Q500, P631, S817, A518, A519, S820, S821, S822, S823, S824, P825, ME26, T827, E843, N844, F545, V546, H547, V548, H549, V555, M856, E557, Y568, T568, B79, T880, N881, H882, F583, G884, S585, T886, Y687, S689, H889 | 42 | 0.788 |
| 3 | V697, P698, L699, E700, D701, R702, V703, V704, S705, V706, G707, E708, T709, V710, A711, F727, K728, G729, D730, R731, P732, L733, G734, L736, T738, E737, R738, H739, H740, L741, T742, P743, D744, N745, L747, V749, V750, Q751, N752, V753, N754, A755, E755, D757, A758, R760, Q777, L778, S779, V780, L781, L782, E783 | 53 | 0.739 |
| 4 | D811, K831, K832, D833, M834, E835, V836, L837, T838, N839, A840, D841, M842, H843, R845 | 15 | 0.669 |
| 5 | T614, M615, H849, V850, M651, P852, D853, D954, D985, V856, F856, T860 | 12 | 0.669 |
| 6 | V608, G809, K510, Q888, V867, T668, F969, G970 | 8 | 0.529 |

[FIG. 4]

[FIG. 5]
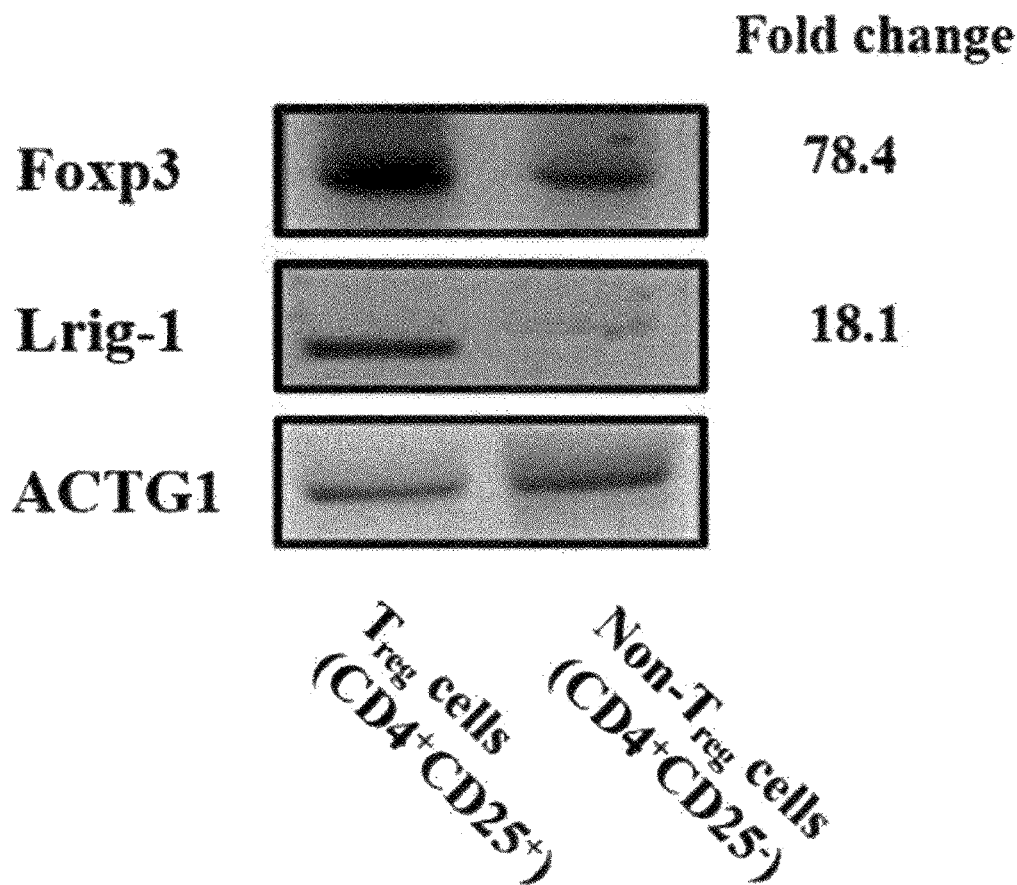

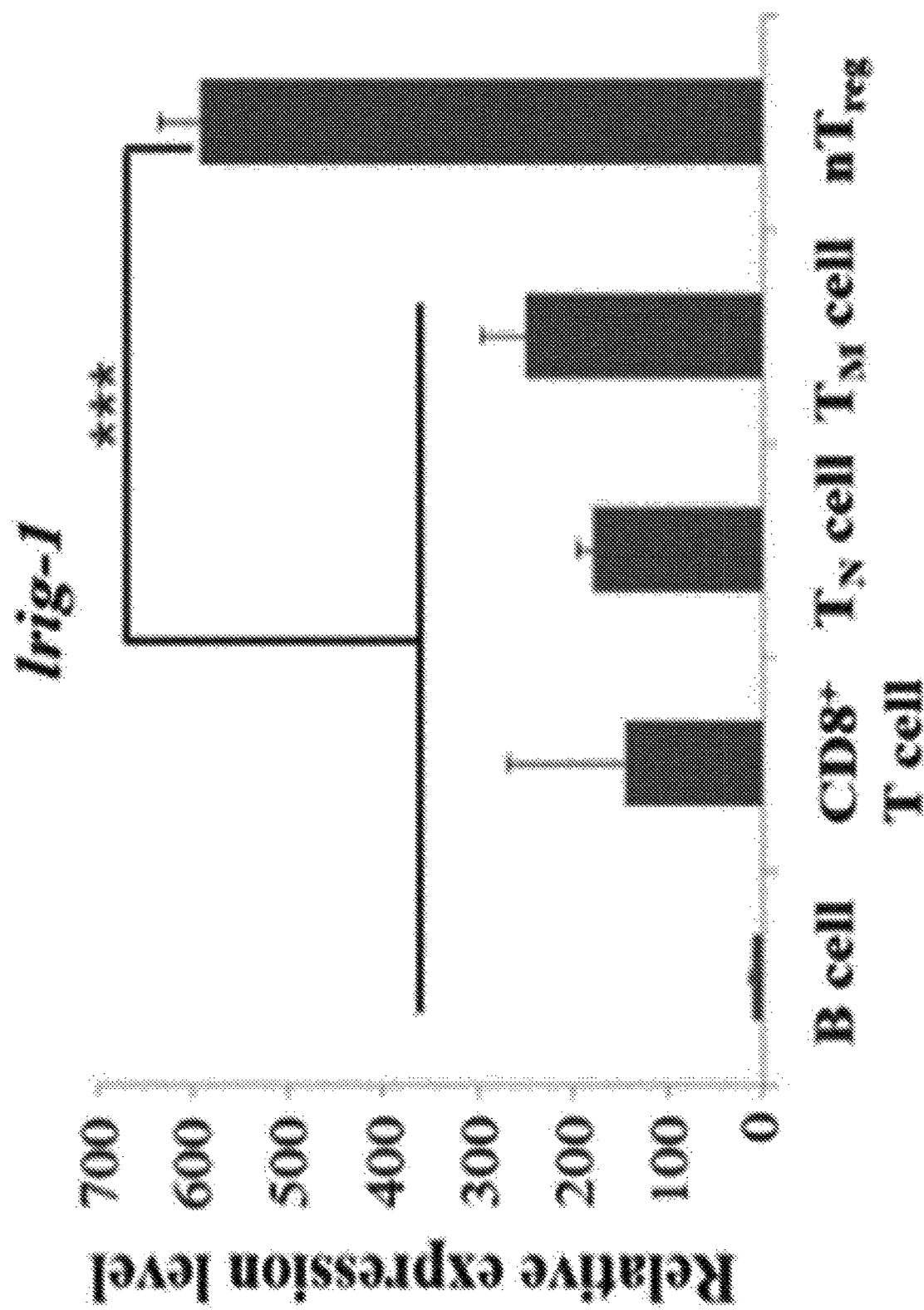
[FIG. 6]

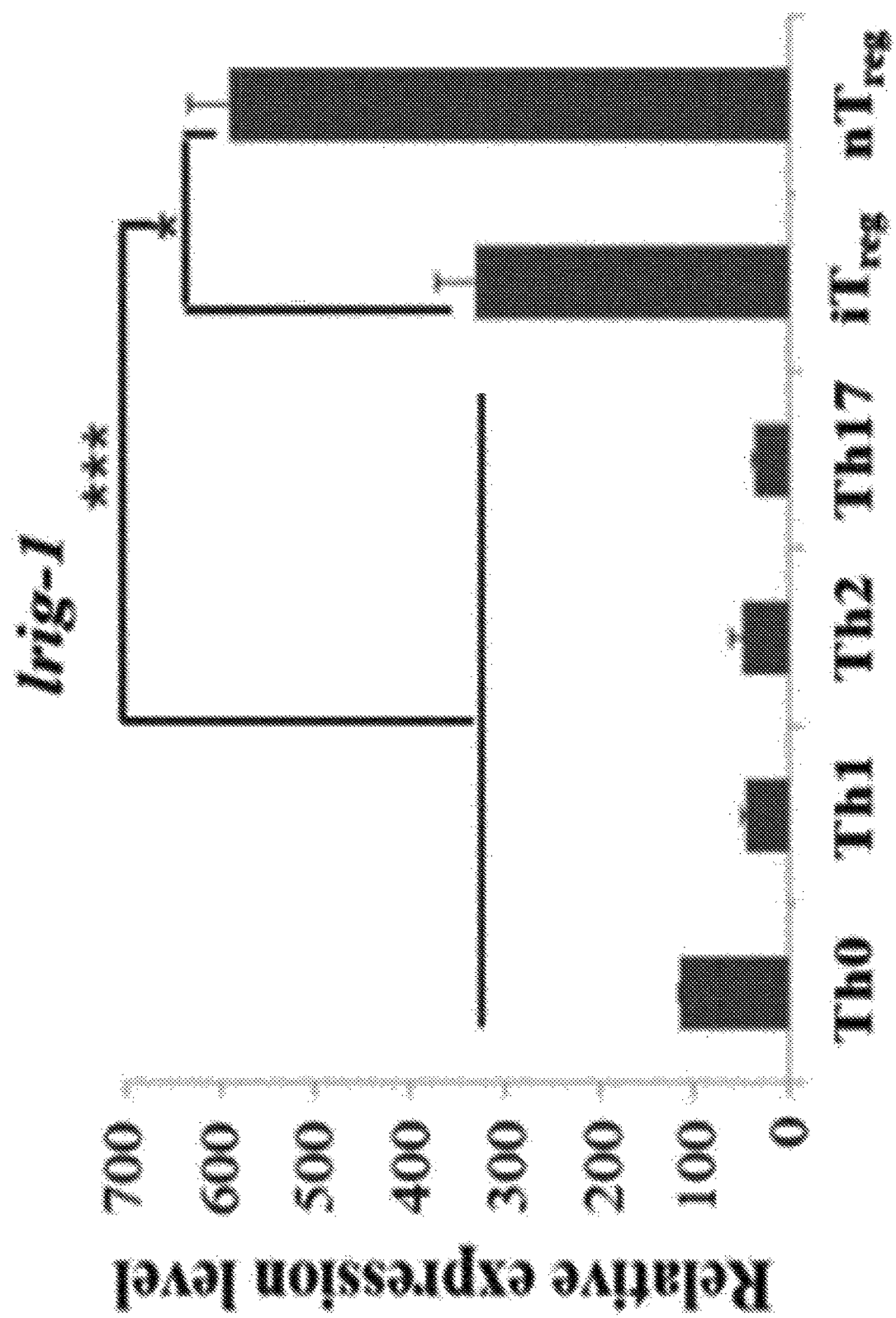
[FIG. 7]

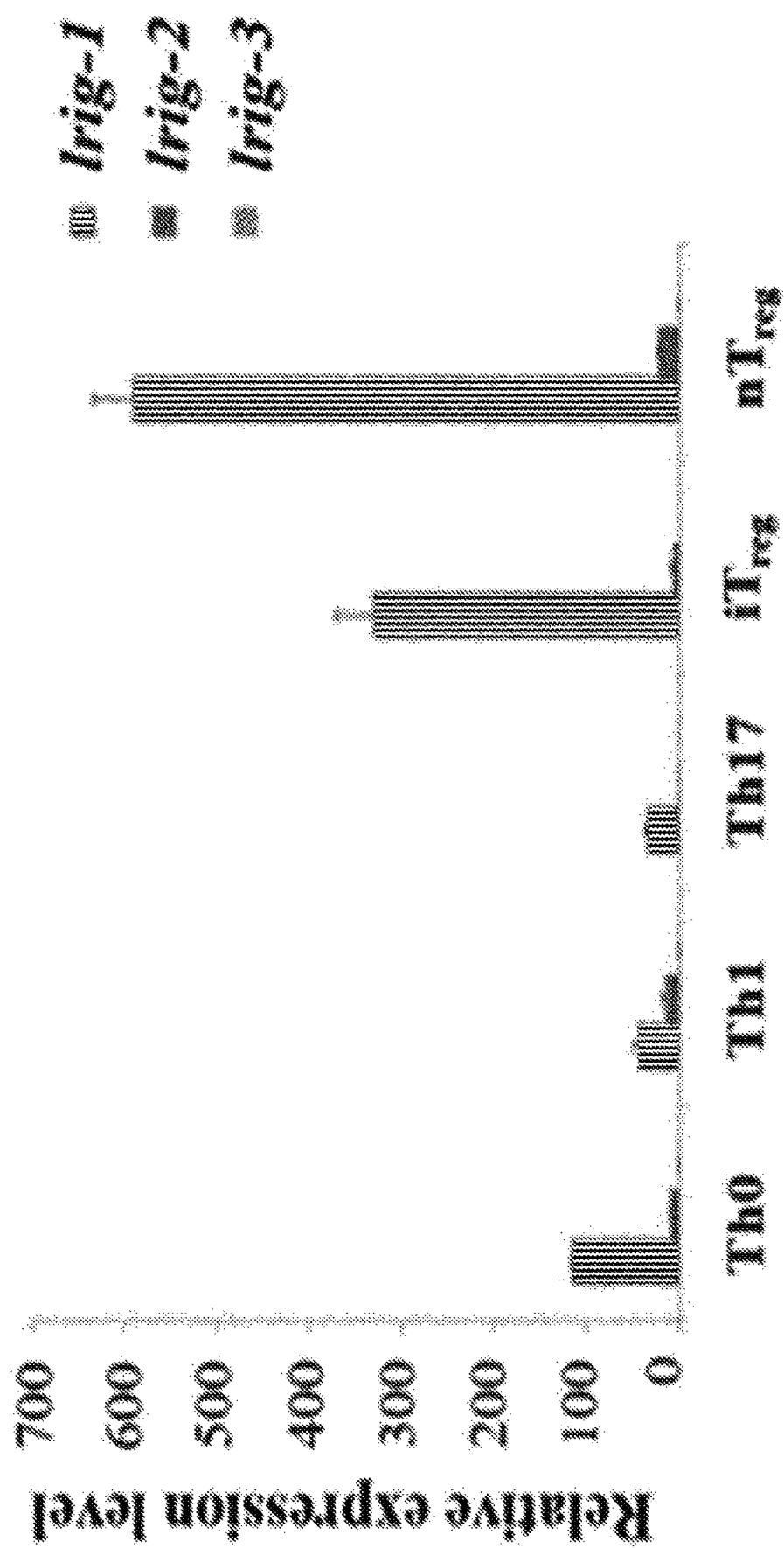
[FIG. 8]

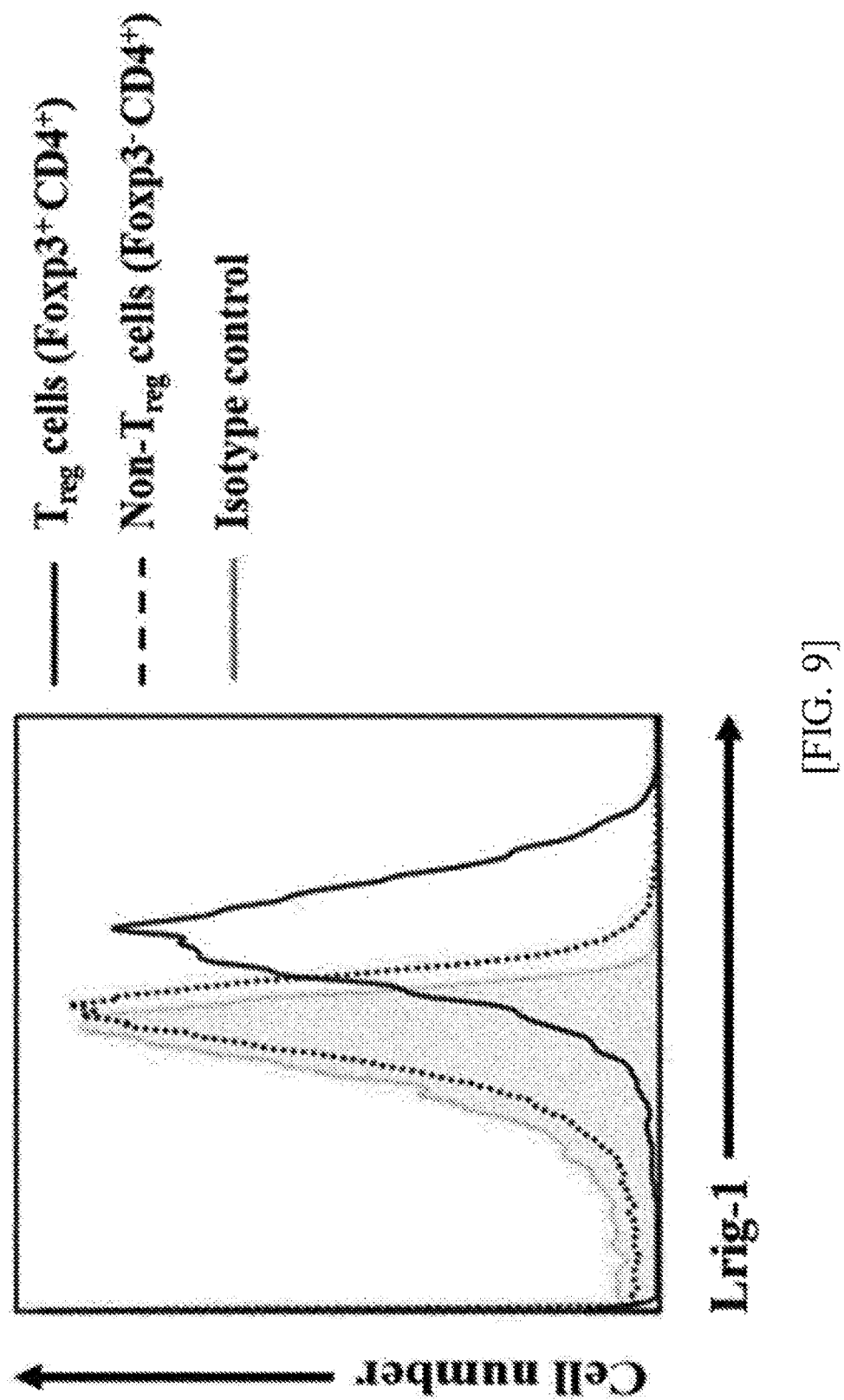
[FIG. 9]

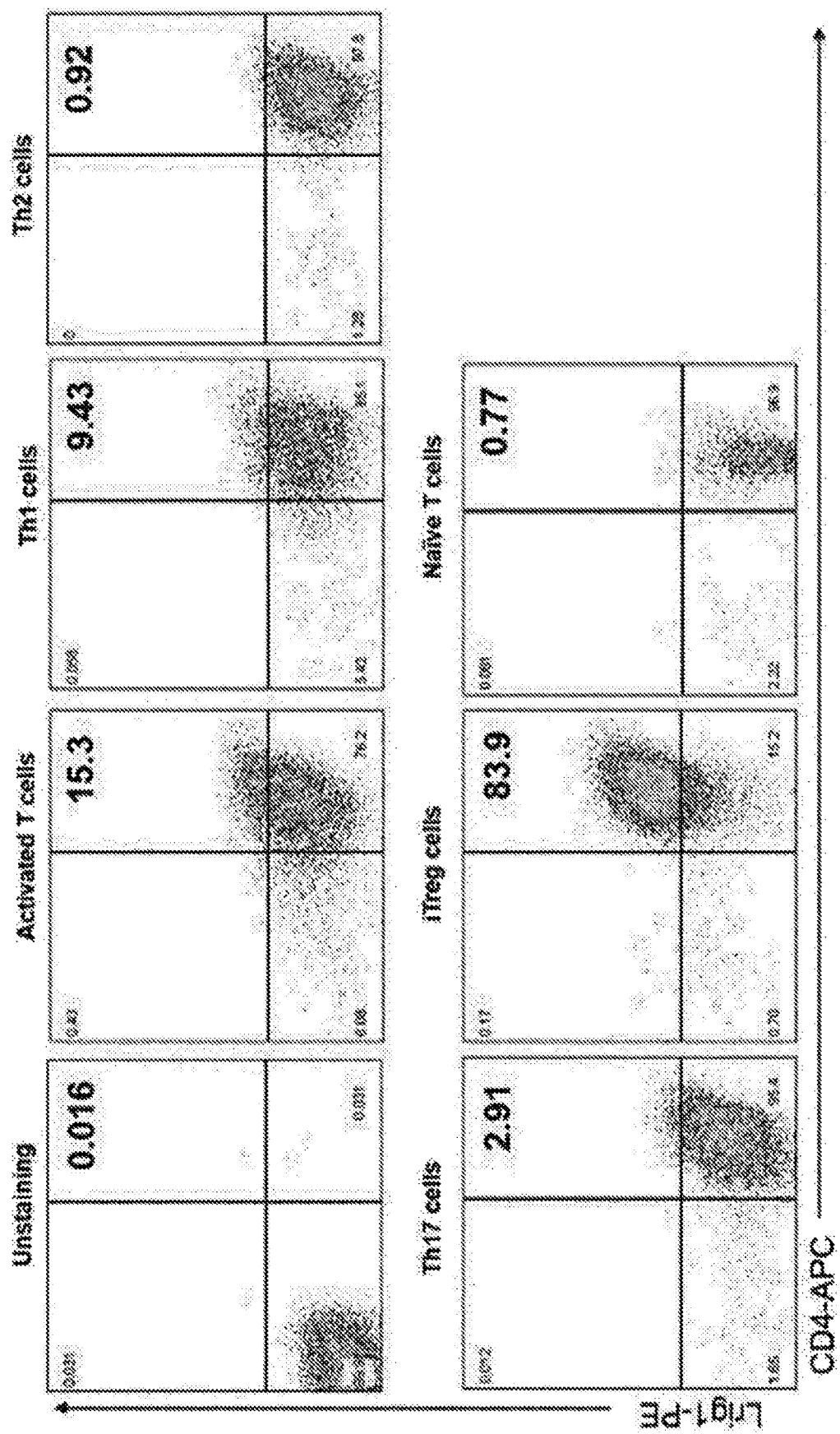
[FIG. 10]

[FIG. 11]
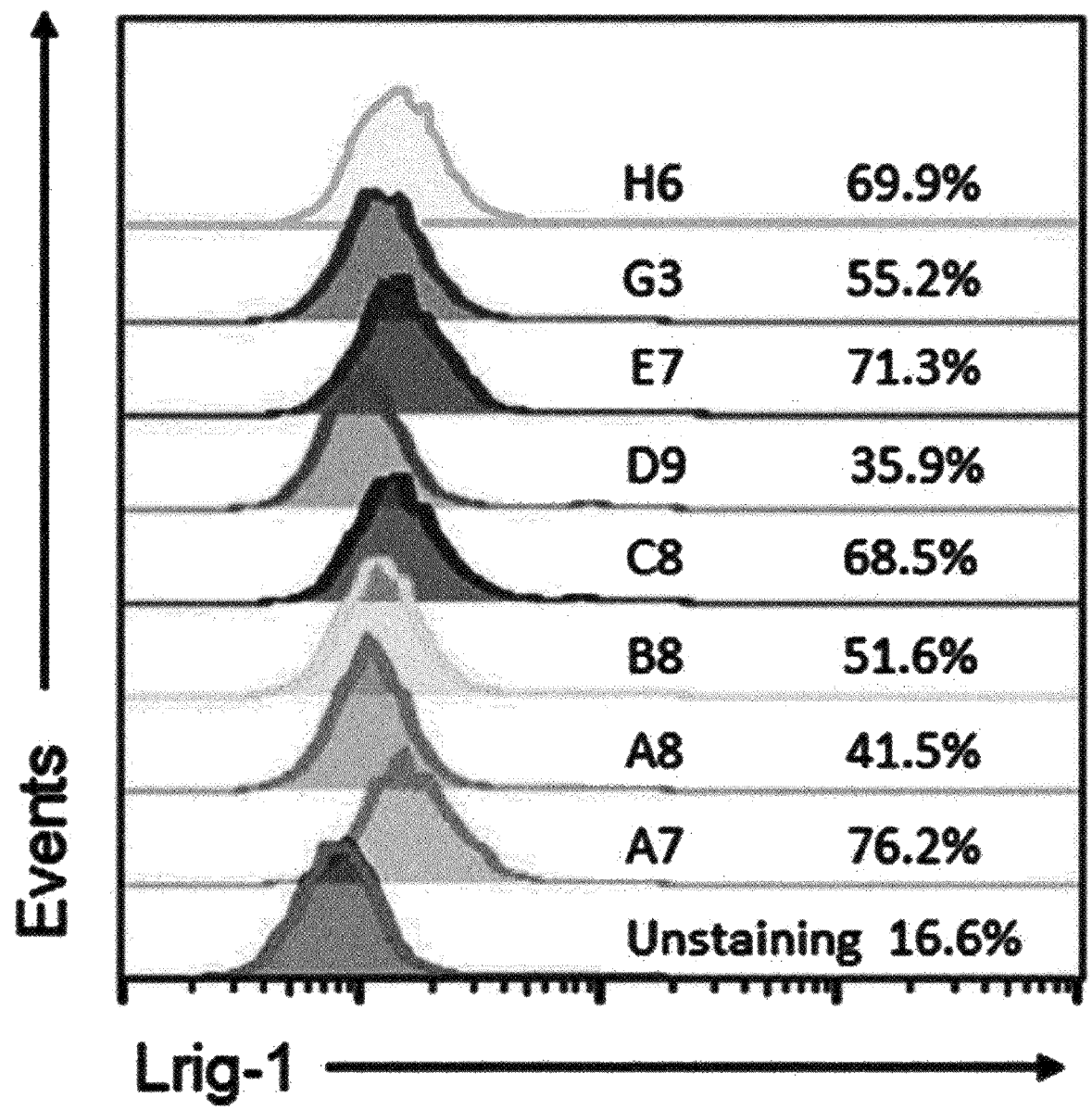

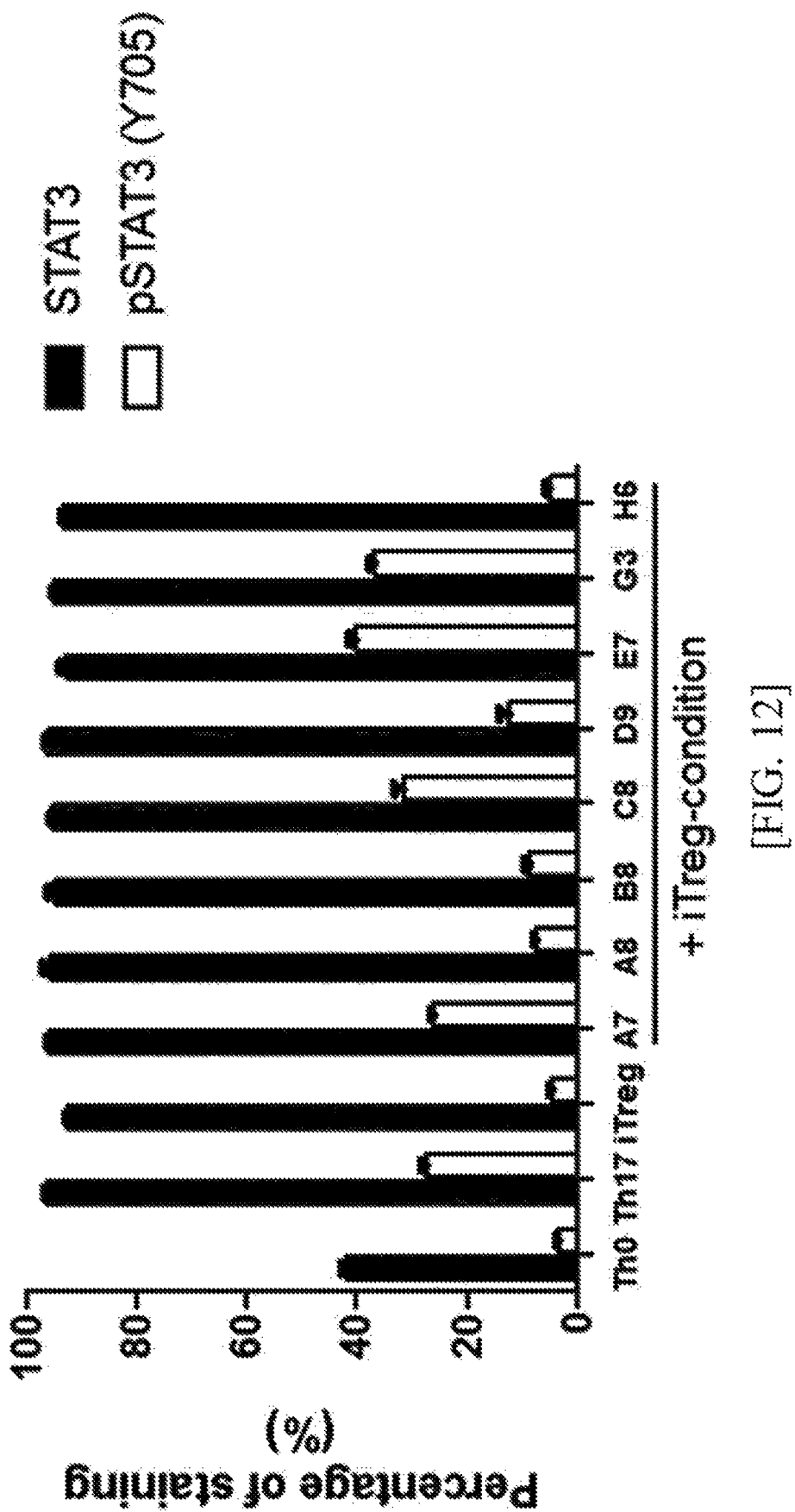
[FIG. 12]

[FIG. 13]
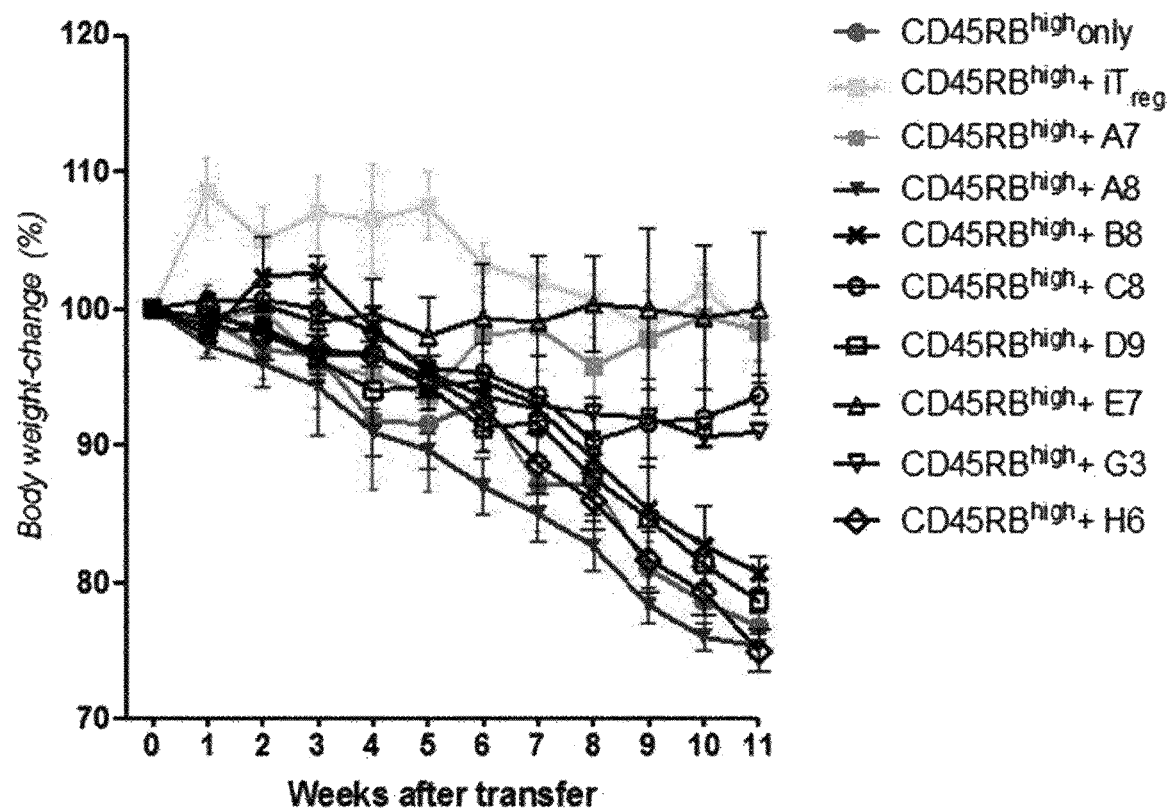

BINDING MOLECULE SPECIFIC FOR LRIG-1 PROTEIN AND USE THEREOF

CROSS REFERENCE TO RELATED APPLICATIONS

This application is a U.S. National Stage of International Application No. PCT/KR2018/004523, filed Apr. 18, 2018, which claims the benefit of Korean Patent Application No. 10-2017-0049854, filed Apr. 18, 2017, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "54874_Seglisting.txt." The Sequence Listing was created on Oct. 17, 2019, and is 78,651 bytes in size. The subject matter of the Sequence Listing is incorporated herein in its entirety by reference.

TECHNICAL FIELD

The present invention relates to a binding molecule capable of specifically binding to leucine-rich and immunoglobulin-like domains 1 (Lrig-1) protein, which is a protein present on the surface of regulatory T cells (Treg cells), and a use thereof.

BACKGROUND ART

One of the most important traits in all normal individuals is to have the ability to recognize and eliminate non-self antigens, while not detrimentally responding to antigenic substances that make up the self. As such, non-response of the living body to self antigens is called immunologic unresponsiveness or tolerance. Self-tolerance occurs by eliminating lymphocytes that may have specific receptors for self antigens, or by self-inactivation of the ability to respond after contacting self antigens. In a case where a problem arises in inducing or maintaining self-tolerance, an immune response to self antigens occurs, and the disease resulting therefrom is called autoimmune disease.

For the treatment of the autoimmune disease, a concept of suppressor T cells suggesting the possibility of presence of T cells capable of controlling and suppressing the effector function of conventional T cells was introduced and presented for the first time by Gershon in the early 1970s (R. K. Gershon and K. Kondo, Immunology, 1970, 18: 723-37). Since then, studies have been conducted to elucidate biological properties and functions of regulatory T cells in many areas of immunology.

In this connection, it has been reported that the regulatory T cells (Treg cells) play an important role in naturally preventing occurrence of excessive inflammation and immune responses; however, in a case where autoimmune disease and a chronic inflammatory disease occur, the function and the number of the regulatory T cells are remarkably decreased. Therefore, in a case of patients with immune and inflammatory diseases, it is important that the regulatory T cells are produced at a normal level, which can be one of the treatments for these diseases.

Until now, studies on genes and proteins which are present specifically in regulatory T cells have been conducted, and it has been presented that substances such as CD25, CTLA4, CD62L, CD38, CD103, GITR, and CD45RB may correspond to marker substances. However, there are no genes and proteins that can target only the regulatory T cells alone.

On the other hand, there are three hypervariable regions called complementarity determining regions (hereinafter referred to as "CDRs") and four framework regions. The CDRs primarily serve to bind to an epitope on an antigen. The CDRs of each chain are typically referred to as CDR1, CDR2, and CDR3 sequentially starting from the N-terminus, and are also distinguished by the chain where particular CDRs are located.

Technical Problem

An object of the present invention is to provide a binding molecule specific for Lrig-1 protein present on the surface of regulatory T cells (Treg cells).

Another object of the present invention is to provide a nucleic acid molecule which encodes the binding molecule according to the present invention.

Yet another object of the present invention is to provide an expression vector into which the nucleic acid molecule according to the present invention is inserted.

Still yet another object of the present invention is to provide a host cell line transfected with the expression vector according to the present invention.

Still yet another object of the present invention is to provide an antibody-drug conjugate according to the present invention.

Still yet another object of the present invention is to provide a pharmaceutical composition for preventing or treating immune-related diseases, comprising the binding molecule according to the present invention.

However, the technical problem to be solved by the present invention is not limited to the above-mentioned problems, and other problems which are not mentioned will be clearly understood by those skilled in the art from the following description.

Solution to Problem

The present inventors have discovered Lrig-1 protein that is present specifically on the surface of regulatory T cells, have selected an epitope on the protein, and have produced a monoclonal antibody capable of specifically binding to the Lrig-1 protein, thereby completing the present invention.

According to an embodiment of the present invention, there is provided a binding molecule which specifically binds to leucine-rich and immunoglobulin-like domains 1 (Lrig-1) protein.

As used herein, the term "binding molecule" refers to a variable domain comprising an intact immunoglobulin that includes a monoclonal antibody, such as a chimeric, humanized, or human monoclonal antibody, or an immunoglobulin that binds to an antigen, for example, an immunoglobulin fragment that competes with intact immunoglobulins for binding to monomeric HA or trimeric HA of influenza A virus. Regardless of the structure, an antigen-binding fragment binds to the same antigen recognized by intact immunoglobulins. The antigen-binding fragment may include a peptide or polypeptide which contains, out of the amino acid sequence of the binding molecule, an amino acid sequence of two or more contiguous residues, 20 or more contiguous amino acid residues, 25 or more contiguous amino acid residues, 30 or more contiguous amino acid residues, 35 or more contiguous amino acid residues, 40 or more contiguous amino acid residues, 50 or more contiguous amino acid residues, 60 or more contiguous amino acid residues, 70 or more contiguous amino acid residues, 80 or more contiguous amino acid residues, 90 or more contiguous amino acid residues, 100 or more contiguous amino acid residues, 125 or more contiguous amino acid residues, 150 or more contiguous amino acid residues, 175 or more contiguous amino acid residues, 200 or more contiguous amino acid residues, or 250 or more contiguous amino acid residues. The term "antigen-binding fragment", in particular, includes Fab, F(ab'), F(ab')2, Fv, dAb, Fd, complementarity determining region (CDR) fragments, single-chain antibodies (scFvs), bivalent single-chain antibodies, single-chain phage antibodies, diabodies, triabodies, tetrabodies, polypeptides containing one or more fragments of immunoglobulin which is sufficient for a particular antigen to bind to the polypeptide, and the like. The fragment may be produced synthetically or by enzymatic or chemical digestion of a complete immunoglobulin, or may be produced by genetic engineering methods using recombinant DNA techniques. Production methods are well known in the art.

In the present invention, the Lrig-1 protein is a transmembrane protein consisting of 1091 amino acids present on the surface of regulatory T cells, and is composed of leucine-rich repeats (LRRs) and three immunoglobulin-like domains on the extracellular or lumen side, a cell transmembrane sequence, and a cytoplasmic tail portion. The LRIG gene family includes LRIG1, LRIG2, and LRIG3, and the amino acids therebetween are highly conserved. The LRIG1 gene is highly expressed in normal skin and can be expressed in basal and hair follicle cells to regulate proliferation of epithelial stem cells. Therefore, the LRIG1 gene plays an important role in maintaining homeostasis of the epidermis, and its absence may develop psoriasis or skin cancer. It has been reported that in a case where chromosome 3p14.3 portion in which LRIG1 is located is cut off, there is a possibility of developing into cancer cells. In fact, it was identified that expression of LRIG1 is greatly decreased in renal cell carcinoma and cutaneous squamous cell carcinoma. Recently, it has been also found that Lrig-1 is expressed in only about 20 to 30% of cancers. On the other hand, for the purpose of the present invention, the Lrig-1 protein may be, but is not limited to, a protein present in humans or mice.

In the present invention, the Lrig-1 protein may be, but is not limited to, a human-derived polypeptide represented by SEQ ID NO: 1 or a mouse-derived polypeptide represented by SEQ ID NO: 3.

In addition, in the present invention, the Lrig-1 protein represented by SEQ ID NO: 1 may be encoded by a polynucleotide represented by SEQ ID NO: 2, but is not limited thereto.

In addition, in the present invention, the Lrig-1 protein represented by SEQ ID NO: 3 may be encoded by a polynucleotide represented by SEQ ID NO: 4, but is not limited thereto.

In the present invention, the binding molecule may be a binding molecule, comprising:

a heavy chain variable region that contains a heavy chain CDR1 consisting of an amino acid sequence selected from the group consisting of SEQ ID NOs: 5, 13, 21, and 29; a heavy chain CDR2 consisting of an amino acid sequence selected from the group consisting of SEQ ID NOs: 6, 14, 22, and 30; a heavy chain CDR3 consisting of an amino acid sequence selected from the group consisting of SEQ ID NOs: 7, 15, 23, and 31; and a light chain variable region that contains a light chain CDR1 consisting of an amino acid sequence selected from the group consisting of SEQ ID NOs: 8, 16, 24, and 32; a light chain CDR2 consisting of an amino acid sequence selected from the group consisting of SEQ ID NOs: 9, 17, 25, and 33; a light chain CDR3 consisting of an amino acid sequence selected from the group consisting of SEQ ID NO: 10, 18, 26, and 34.

In the present invention, the binding molecule may be a binding molecule, comprising:

a heavy chain variable region, selected from the group consisting of the following (a) to (d):

(a) a heavy chain variable region that contains a heavy chain CDR1 represented by SEQ ID NO: 5, a heavy chain CDR2 represented by SEQ ID NO: 6, and a heavy chain CDR3 represented by SEQ ID NO: 7;

(b) a heavy chain variable region that contains a heavy chain CDR1 represented by SEQ ID NO: 13, a heavy chain CDR2 represented by SEQ ID NO: 14, and a heavy chain CDR3 represented by SEQ ID NO: 15;

(c) a heavy chain variable region that contains a heavy chain CDR1 represented by SEQ ID NO: 21, a heavy chain CDR2 represented by SEQ ID NO: 22, and a heavy chain CDR3 represented by SEQ ID NO: 23; and (d) a heavy chain variable region that contains a heavy chain CDR1 represented by SEQ ID NO: 29, a heavy chain CDR2 represented by SEQ ID NO: 30, and a heavy chain CDR3 represented by SEQ ID NO: 31; and a light chain variable region, selected from the group consisting of the following (e) to (h):

(e) a light chain variable region that contains a light chain CDR1 represented by SEQ ID NO: 8, a light chain CDR2 represented by SEQ ID NO: 9, and a light chain CDR3 represented by SEQ ID NO: 10;

(f) a light chain variable region that contains a light chain CDR1 represented by SEQ ID NO: 16, a light chain CDR2 represented by SEQ ID NO: 17, and a light chain CDR3 represented by SEQ ID NO: 18;

(g) a light chain variable region that contains a light chain CDR1 represented by SEQ ID NO: 24, a light chain CDR2 represented by SEQ ID NO: 25, and a light chain CDR3 represented by SEQ ID NO: 26;

(h) a light chain variable region that contains a light chain CDR1 represented by SEQ ID NO: 32, a light chain CDR2 represented by SEQ ID NO: 33, and a light chain CDR3 represented by SEQ ID NO: 34.

In the present invention, the binding molecule may be a binding molecule selected from the group consisting of the following (1) to (4):

(1) a binding molecule comprising a heavy chain variable region that contains a heavy chain CDR1 represented by SEQ ID NO: 5, a heavy chain CDR2 represented by SEQ ID NO: 6, and a heavy chain CDR3 represented by SEQ ID NO: 7; and a light chain variable region that contains a light chain CDR1 represented by SEQ ID NO: 8, a light chain CDR2 represented by SEQ ID NO: 9, and a light chain CDR3 represented by SEQ ID NO: 10;

(2) a binding molecule comprising a heavy chain variable region that contains a heavy chain CDR1 represented by SEQ ID NO: 13, a heavy chain CDR2 represented by SEQ ID NO: 14, and a heavy chain CDR3 represented by SEQ ID NO: 15; and a light chain variable region that contains a light chain CDR1 represented by SEQ ID NO: 16, a light chain CDR2 represented by SEQ ID NO: 17, and a light chain CDR3 represented by SEQ ID NO: 18;

(3) a binding molecule comprising a heavy chain variable region that contains a heavy chain CDR1 represented by SEQ ID NO: 21, a heavy chain CDR2 represented by SEQ ID NO: 22, and a heavy chain CDR3 represented by SEQ ID NO: 23; and a light chain variable region that contains a light chain CDR1 represented by SEQ ID NO: 24, a light chain CDR2 represented by SEQ ID NO: 25, and a light chain CDR3 represented by SEQ ID NO: 26;

(4) a binding molecule comprising a heavy chain variable region that contains a heavy chain CDR1 represented by SEQ ID NO: 29, a heavy chain CDR2 represented by SEQ ID NO: 30, and a heavy chain CDR3 represented by SEQ ID NO: 31; and a light chain variable region that contains a light chain CDR1 represented by SEQ ID NO: 32, a light chain CDR2 represented by SEQ ID NO: 33, and a light chain CDR3 represented by SEQ ID NO: 34.

In the present invention, the binding molecule may be a binding molecule, comprising:

a heavy chain variable region consisting of any one amino acid sequence selected from the group consisting of SEQ ID NOs: 11, 19, 27, and 35; and a light chain variable region consisting of any one amino acid sequence selected from the group consisting of SEQ ID NO: 12, 20, 28, and 36.

In the present invention, the binding molecule may be a binding molecule selected from the group consisting of the following binding molecules:

a binding molecule comprising a heavy chain variable region represented by SEQ ID NO: 11, and a light chain variable region represented by SEQ ID NO: 12;

a binding molecule comprising a heavy chain variable region represented by SEQ ID NO: 19, and a light chain variable region represented by SEQ ID NO: 20;

a binding molecule comprising a heavy chain variable region represented by SEQ ID NO: 27, and a light chain variable region represented by SEQ ID NO: 28; and a binding molecule comprising a heavy chain variable region represented by SEQ ID NO: 35, and a light chain variable region represented by SEQ ID NO: 36.

In the present invention, the binding molecule may further comprise a fragment crystallization (Fc) region or a constant region. Here, the Fc region may be an Fc region of an IgG1, IgG2, IgG3, or IgG4 antibody, or may be derived therefrom. Alternatively, the Fc region may be a hybrid Fc region.

As an example of the present invention, the constant region may be a mouse-derived IgG2a constant region represented by SEQ ID NO: 37, but is not limited thereto.

As an example of the present invention, the constant region may be a mouse-derived immunoglobulin kappa constant region represented by SEQ ID NO: 38.

As an example of the present invention, the constant region may be a human-derived IgG1 constant region represented by SEQ ID NO: 39.

As an example of the present invention, the constant region may be a human-derived immunoglobulin kappa constant region represented by SEQ ID NO: 40, but is not limited thereto.

As an example of the present invention, the constant region may be a human-derived IgG2 constant region represented by SEQ ID NO: 41, but is not limited thereto.

As an example of the present invention, the constant region may be a human-derived IgG3 constant region represented by SEQ ID NO: 42, but is not limited thereto.

As an example of the present invention, the constant region may be a human-derived IgG4 constant region represented by SEQ ID NO: 43, but is not limited thereto.

As an example of the present invention, the Fc region may be a human-derived immunoglobulin kappa constant region represented by SEQ ID NO: 43, but is not limited thereto.

As an example of the present invention, the Fc region may be a human-derived immunoglobulin lambda constant region, but is not limited thereto.

In the present invention, the "hybrid Fc" may be derived from a combination of human IgG subclasses or a combination of human IgD and IgG. In a case where the hybrid Fc binds to a biologically active molecule, polypeptide, or the like, the hybrid Fc has effects of not only increasing a serum half-life of the biologically active molecule, but also increasing an expression level of the polypeptide when a nucleotide sequence encoding the Fc-polypeptide fusion protein is expressed.

As an example of the present invention, the hybrid Fc region may be represented by SEQ ID NO: 44, but is not limited thereto.

In the binding molecule of the present invention, the Fc or constant region may be linked, via a linker, to the variable region. Here, the linker may be linked to the C-terminus of the Fc, and the N-terminus of the binding molecule of the present invention may be linked to the linker. However, the present invention is not limited thereto.

In the present invention, the "linker" may contain a sequence that can be cleaved by an enzyme that is overexpressed in a tissue or cell having a target disease. In a case where the linker may be cleaved by the overexpressed enzyme as described above, it is possible to effectively prevent activity of a polypeptide from decreasing due to the Fc portion. In the present invention, an example of the linker may be preferably a peptide linker consisting of 33 amino acids located in the $282^{nd}$ to $314^{th}$ portion of human albumin which is most abundantly present in the blood, and more preferably a peptide linker consisting of 13 amino acids located in the $292^{nd}$ to $304^{th}$ portion of the human albumin. Such portions are portions which are mostly exposed to the outside in three-dimensional structure, and thus has a minimum possibility of inducing an immune response in the body. However, the linker is not limited thereto.

The binding molecule of the present invention may further comprise a heavy chain constant region consisting of an amino acid sequence selected from the group consisting of SEQ ID NOs: 37, 39, 41, 42, 43, and 44.

The binding molecule of the present invention may further comprise a light chain constant region consisting of an amino acid sequence represented by SEQ ID NO: 38 or 40.

The binding molecule of the present invention may further comprise:

a heavy chain constant region consisting of an amino acid sequence represented by SEQ ID NO: 37; and a light chain constant region consisting of an amino acid sequence represented by SEQ ID NO: 38.

The binding molecule of the present invention may further comprise:

a heavy chain constant region consisting of an amino acid sequence represented by SEQ ID NO: 39, 41, 42, or 43; and a light chain constant region consisting of an amino acid sequence represented by SEQ ID NO: 40.

The binding molecule of the present invention may further comprise:

a heavy chain constant region consisting of an amino acid sequence represented by SEQ ID NO: 44.

The binding molecule of the present invention may be a binding molecule selected from the group of the following binding molecules:

a binding molecule comprising a heavy chain represented by SEQ ID NO: 45, and a light chain represented by SEQ ID NO: 46;

a binding molecule comprising a heavy chain represented by SEQ ID NO: 47, and a light chain represented by SEQ ID NO: 48;

a binding molecule comprising a heavy chain represented by SEQ ID NO: 49, and a light chain represented by SEQ ID NO: 50; and a binding molecule comprising a heavy chain represented by SEQ ID NO: 51, and a light chain represented by SEQ ID NO: 52.

The binding molecule of the present invention is characterized by being an antibody, but is not limited thereto. The antibody includes all of a monoclonal antibody, a full-length antibody, or an antibody fragment which is a portion of an antibody, has the ability to bind to Lrig-1 protein, and competes with the binding molecule of the present invention in binding to an epitope on Lrig-1.

As used herein, the term "antibody" refers to a protein molecule which serves as a receptor that specifically recognizes an antigen, including an immunoglobulin molecule that is immunologically reactive with a particular antigen. For the purpose of the present invention, the antigen may be Lrig-1 protein present on the surface of regulatory T cells. Preferably, the antibody may specifically recognize the leucine-rich region or immunoglobulin-like domain of the Lrig-1 protein, but is not limited thereto.

In the present invention, the "immunoglobulin" has a heavy chain and a light chain, and each of the heavy chain and the light chain comprises a constant region and a variable region. The variable region of each of the light chain and the heavy chain contains three hypervariable regions called complementarity determining regions (hereinafter referred to as "CDRs") and four framework regions. The CDRs primarily serve to bind to an epitope on an antigen. The CDRs of each chain are typically referred to as CDR1, CDR2, and CDR3 sequentially starting from the N-terminus, and are also distinguished by the chain where particular CDRs are located.

In addition, as used herein, the term "monoclonal antibody" refers to an antibody molecule of a single molecular composition which is obtained from substantially the same antibody population, and exhibits single binding specificity and affinity for a particular epitope.

In the present invention, the "full-length antibody" has a structure with two full-length light chains and two full-length heavy chains in which each light chain is linked to a heavy chain by disulfide bond, and includes IgA, IgD, IgE, IgM, and IgG. The IgG includes, as subtypes thereof, IgG1, IgG2, IgG3, and IgG4.

In addition, as used herein, the term "antigen fragment" refers to a fragment that retains an antigen-binding function, and includes Fab, Fab', F(ab')$_2$, Fv, and the like. The Fab has a structure with variable regions of light and heavy chains, a constant region of the light chain, and a first constant region (CH1 domain) of the heavy chain, and has one antigen-binding site. In addition, Fab' is different from Fab in that Fab' has a hinge region containing at least one cysteine residue at the C-terminus of the heavy chain CH1 domain. F(ab')$_2$ antibodies are produced with cysteine residues at the hinge region of Fab' forming disulfide bond. Fv (variable fragment) refers to the smallest antibody fragment having only a heavy chain variable region and a light chain variable region. Double-chain Fv (dsFv) is configured to be such that a heavy chain variable region and a light chain variable region are linked to each other by disulfide bond, and single-chain Fv (scFv) is configured to be such that a heavy chain variable region and a light chain variable region are covalently linked to each other, in general, via a peptide linker. The antibody fragment may be obtained as Fab or F(ab')$_2$ fragment in a case where a proteolytic enzyme, for example, papain or pepsin is used, and may be produced through a genetic recombinant technique.

In addition, in the present invention, the antibody may be, but is not limited to, a chimeric antibody, a humanized antibody, a bivalent, bispecific molecule, a minibody, a domain antibody, a bispecific antibody, an antibody mimetic, a diabody, a triabody, or a tetrabody, or a fragment thereof.

In the present invention, the "chimeric antibody" is an antibody which is obtained by recombination of a variable region of a mouse antibody and a constant region of a human antibody, and has a greatly improved immune response as compared with the mouse antibody.

In addition, as used herein, the term "humanized antibody" refers to an antibody obtained by modifying a protein sequence of an antibody derived from a non-human species so that the protein sequence is similar to an antibody variant naturally produced in humans. For example, the humanized antibody may be prepared as follows. Mouse-derived CDRs may be recombined with a human antibody-derived FR to prepare a humanized variable region, and the humanized variable region may be recombined with a constant region of a preferred human antibody to prepare a humanized antibody. In the present invention, the binding molecule may be provided as a bispecific antibody or a bispecific antigen-binding fragment which is capable of binding to Lrig-1 protein and also binding to another protein.

In the present invention, the bispecific antibody and the bispecific antigen-binding fragment may comprise the binding molecule according to the present invention. As an example of the present invention, the bispecific antibody and the bispecific antigen-binding fragment comprise an antigen-binding domain capable of binding to Lrig-1 protein, wherein the antigen-binding domain capable of binding to Lrig-1 protein may comprise or consist of the binding molecule according to the present invention.

The bispecific antibody and the bispecific antigen-binding fragment provided in the present invention comprise an antigen-binding domain, which is a binding molecule capable of binding to Lrig-1 protein according to the present invention, and an antigen-binding domain capable of binding to another target protein. Here, the antigen-binding domain capable of binding another target protein may be an antigen-binding domain capable of binding to a protein other than Lrig-1 protein, for example, but not limited to, PD-1 or a cell surface receptor. However, the antigen-binding domain is not limited thereto.

The bispecific antibody and the bispecific antigen-binding fragment according to the present invention may be provided in any suitable format, for example, that described in Kontermann MAbs 2012, 4(2): 182-197, which is incorporated herein by reference in its entirety. For example, the bispecific antibody or the bispecific antigen-binding fragment may be a bispecific antibody conjugate (for example, IgG2, F(ab')2, or CovX-body), a bispecific IgG or IgG-like molecule (for example, IgG, scFv4-Ig, IgG-scFv, scFv-IgG, DVD-Ig, IgG-sVD, sVD-IgG, or 2 in 1-IgG, mAb2, or Tandemab common LC), an asymmetric bispecific IgG or IgG-like molecule (for example, kih IgG, kih IgG common LC, CrossMab, kih IgG-scFab, mAb-Fv, charge pair, or SEED-body), a small bispecific antibody molecule (for example, diabody (Db), dsDb, DART, scDb, tandAb, tandem scFv (taFv), tandem dAb/VHH, triple body, triple head, Fab-scFv, or F(ab')2-scFv2), a bispecific Fc and CH3 fusion protein (for example, taFv-Fc, di-diabody, scDb-CH3, scFv- Fc-scFv, HCAb-VHH, scFv-kih-Fc, or scFv-kih-CH3), or a bispecific fusion protein (for example, scFv2-albumin, scDb-albumin, taFv-toxin, DNL-Fab3, DNL-Fab4-IgG, DNL-Fab4-IgG-cytokine 2). See, in particular, FIG. 2 in Kontermann MAbs 2012, 4(2): 182-19. The bispecific antibody and the bispecific antigen-binding fragment according to the invention may be designed and prepared by those skilled in the art.

A method for producing the bispecific antibody in the present invention comprises forming a reducing disulfide or non-reducing thioether bond, and chemical crosslinking of an antibody or antibody fragment as described, for example, in Segal and Bast, 2001. Production of Bispecific Antibodies. Current Protocols in Immunology. 14:IV:2.13:2.13.1-2.13.16, which is incorporated herein by reference in its entirety. For example, N-succinimidyl-3-(-2-pyridyldithio)-propionate (SPDP) may be used, for example, for chemically crosslinking an Fab fragment through an SH-group at the hinge region, to generate a disulfide-linked bispecific F(ab)2 heterodimer.

In addition, an alternative method for producing the bispecific antibody in the present invention comprises fusing an antibody-producing hybridoma with, for example, polyethylene glycol, to produce quadroma cells capable of secreting bispecific antibodies, as described, for example, in D. M. and Bast, B. J. 2001. Production of Bispecific Antibodies. Current Protocols in Immunology. 14:IV:2.13: 2.13.1-2.13.16.

The bispecific antibody and the bispecific antigen-binding fragment according to the invention may also be, for example, recombinantly produced by expression from a nucleic acid construct that encodes a polypeptide for an antigen-binding molecule, as described, for example, in Antibody Engineering: Methods and Protocols, Second Edition (Humana Press, 2012), at Chapter 40: Production of Bispecific Antibodies: Diabodies and Tandem scFv (Hornig and Farber-Schwarz), or French, How to make bispecific antibodies, Methods Mol. Med. 2000; 40:333-339, both of which are incorporated herein by reference in their entireties.

For example, a DNA construct that contains a sequence encoding light and heavy chain variable domains for two antigen-binding domains (that is, light and heavy chain variable domains for an antigen-binding domain capable of binding to PD-1, and light and heavy chain variable domains for an antigen-binding domain capable of binding to another target protein), and a sequence encoding a suitable linker or dimerization domain between the antigen-binding domains may be prepared by molecular cloning techniques. Subsequently, a recombinant bispecific antibody may be produced by expression of the construct (for example, in vitro) in a suitable host cell (for example, a mammalian host cell), and then the expressed recombinant bispecific antibody may be optionally purified.

Antibodies may be produced by an affinity maturation process in which a modified antibody with improved affinity for an antigen as compared with an unmodified parent antibody is produced. An affinity matured antibody may be produced by a procedure known in the art, for example, in Marks et al., Rio/Technology 10:779-783 (1992); Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7): 3310-159 (1995); and Hawkins et al, J. Mol. Biol. 226:889-896 (1992).

In addition, the binding molecule provided in the present invention may include a variant of the amino acid sequence as long as the variant can specifically bind to Lrig-1 protein. For example, in order to improve binding affinity and/or other biological properties of an antibody, modifications may be made to an amino acid sequence of the antibody. Such modifications include, for example, deletions, insertions, and/or substitutions of amino acid sequence residues of the antibody.

Such amino acid variations are made based on relative similarity of amino acid side chain substituents such as hydrophobicity, hydrophilicity, charge, and size. According to analysis on sizes, shapes, and types of amino acid side chain substituents, it can be seen that arginine, lysine, and histidine are all positively charged residues; alanine, glycine, and serine have similar sizes; and phenylalanine, tryptophan, and tyrosine have similar shapes. Thus, based on these considerations, it can be said that arginine, lysine, and histidine; alanine, glycine, and serine; and phenylalanine, tryptophan, and tyrosine are biologically functional equivalents.

In introducing variations, the hydropathic index of amino acids may be considered. Each amino acid has been assigned hydropathic index depending on its hydrophobicity and charge: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The hydropathic amino acid index is very important in conferring the interactive biological function on a protein. It is known that substitution with an amino acid having similar hydropathic index allows a protein to retain similar biological activity. In a case where variations are introduced with reference to the hydropathic index, substitutions are made between amino acids that exhibit a hydropathic index difference of preferably within ±2, more preferably within ±1, and even more preferably within ±0.5.

Meanwhile, it is also well known that substitutions between amino acids having similar hydrophilicity values result in proteins with equivalent biological activity. As disclosed in U.S. Pat. No. 4,554,101, respective amino acid residues have been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In a case where variations are introduced with reference to the hydrophilicity values, substitutions may be made between amino acids that exhibit a hydrophilicity value difference of preferably within ±2, more preferably within ±1, and even more preferably within ±0.5.

Amino acid exchanges in proteins which do not entirely alter activity of a molecule are known in the art (H. Neurath, R. L. Hill, The Proteins, Academic Press, New York (1979)). The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Gln/Glu.

Given the above-described variations with biologically equivalent activity, it is interpreted that the binding molecule of the present invention also includes sequences that exhibit substantial identity with the sequences listed in the Sequence Listing.

As used herein, the term "substantial identity" refers to a sequence showing at least 61% homology, more preferably 70% homology, even more preferably 80% homology, and most preferably 90% homology when the sequence of the present invention is aligned with any other sequence so that they maximally correspond to each other, and the aligned sequence is analyzed by using an algorithm typically used in the art. Alignment methods for comparison of sequences are known in the art. Various methods and algorithms for alignment are disclosed in Smith and Waterman, Adv. Appl. Math. 2:482(1981); Needleman and Wunsch, J. Mol. Bio. 48:443(1970); Pearson and Lipman, Methods in Mol. Biol. 24: 307-31(1988); Higgins and Sharp, Gene 73:237-44 (1988); Higgins and Sharp, CABIOS 5:151-3(1989); Corpet et al., Nuc. Acids Res. 16:10881-90(1988); Huang et al., Comp. Appl. BioSci. 8:155-65(1992); and Pearson et al., Meth. Mol. Biol. 24:307-31(1994). NCBI Basic Local Alignment Search Tool (BLAST) (Altschul et al., J. Mol. Biol. 215: 403-10 (1990)) is accessible from the National Center for Biological Information (NBCI), or the like, and may be used in conjunction with sequencing programs, such as blastp, blasm, blastx, tblastn, and tblastx, on the internet. BLSAT is accessible at www.ncbi.nlm.nih.gov/BLAST/. Sequence homology comparison methods using this program can be identified online (www.ncbi.nlm.nih.gov/BLAST/blast help.html).

In the present invention, the binding molecule, preferably the antibody, may be produced by a conventional method for producing an antibody, and may be produced by affinity maturation.

As used herein, the term "affinity maturation" refers to a process in which antibodies having increased affinity for an antigen are produced by activated B cells in the course of an immune response. For the purpose of the present invention, the affinity maturation allows antibodies or antibody fragments to be produced due to affinity maturation based on the principles of mutation and selection, in the same process that occurs in nature.

The binding molecule, preferably the antibody, provided in the present invention may activate the function, particularly of regulatory T immune cells (Treg cells), among immune cells; increase the number of the Treg cells; and regulate immunological tolerance, thereby effectively preventing, ameliorating, or treating immune-related diseases.

In the present invention, the "immune-related disease" may be a disease induced by excessive activation and expression of various immune cells and inflammatory cells. The immune-related disease may, for example, include autoimmune disease; graft-versus-host diseases; organ transplant rejection; asthma; atopy; or acute or chronic inflammatory disease, but is not limited thereto.

In addition, in the present invention, the "autoimmune disease" may be, but is not limited to, one or more selected from the group consisting of rheumatoid arthritis, systemic scleroderma, systemic lupus erythematosus, atopic dermatitis, psoriasis, alopecia areata, asthma, Crohn's disease, Behcet's disease, Sjogren's syndrome, Guillain-Barré syndrome, chronic thyroiditis, multiple sclerosis, multiple myositis, ankylosing spondylitis, fibrositis, and polyarteritis nodosa.

According to another embodiment of the present invention, there is provided a nucleic acid molecule encoding the binding molecule provided in the present invention.

The nucleic acid molecule of the present invention includes all nucleic acid molecules obtained by translating the amino acid sequences of the binding molecules provided in the present invention to polynucleotide sequences, as known to those skilled in the art. Therefore, various polynucleotide sequences may be prepared by an open reading frame (ORF), and all of these polynucleotide sequences are also included in the nucleic acid molecule of the present invention.

According to yet another embodiment of the present invention, there is provided an expression vector into which the isolated nucleic acid molecule provided in the present invention is inserted.

In the present invention, the "vector" is a nucleic acid molecule capable of transporting another nucleic acid linked thereto. One type of vector is a "plasmid," which refers to circular double-stranded DNA into which an additional DNA segment can be ligated. Another type of vector is a phage vector. Yet another type of vector is a viral vector, where an additional DNA segment can be ligated into the viral genome. Certain vectors are capable of autonomous replication in a host cell into which they are introduced (for example, bacterial vectors having a bacterial origin of replication are episomal mammalian vectors). Other vectors (for example, non-episomal mammalian vectors) can be integrated into the genome of a host cell upon introduction into the host cell, and thus are replicated along with the host genome. In addition, certain vectors are capable of directing expression of genes to which they are operatively linked. Such vectors are referred to herein as "recombinant expression vectors" or simply "expression vectors." In general, expression vectors useful in recombinant DNA techniques are often in the form of plasmids. In the present specification, "plasmid" and "vector" may be used interchangeably as the plasmid is the most commonly used form of vector.

Specific examples of the expression vector in the present invention may be selected from, but are not limited to, the group consisting of commercially widely used pCDNA vectors, F, R1, RP1, Col, pBR322, ToL, Ti vectors; cosmids; phages such as lambda, lambdoid, M13, Mu, p1 P22, Qцц, T-even, T2, T3, T7; plant viruses. Any expression vector known, to those skilled in the art, as expression vectors can be used in the present invention, and the expression vector is selected depending on the nature of the target host cell. Introduction of a vector into a host cell may be performed by calcium phosphate transfection, viral infection, DEAE-dextran-mediated transfection, lipofectamine transfection, or electroporation. However, the present invention is not limited thereto, and those skilled in the art may adopt and use an introduction method appropriate for the expression vector and the host cell which are used. The vector may preferably contain at least one selection marker. However, the present invention is not limited thereto, and selection can be made using the vector that contains no selection marker, depending on whether or not a product is produced. The selection marker is selected depending on the target host cell, which is done using methods already known to those skilled in the art, and thus the present invention has no limitation thereon.

In order to facilitate purification of the nucleic acid molecule of the present invention, a tag sequence may be inserted into and fused to an expression vector. The tag includes, but is not limited to, hexa-histidine tag, hemagglutinin tag, myc tag, or flag tag, and any tag known to those skilled in the art which facilitates purification can be used in the present invention.

According to still yet another embodiment of the present invention, there is provided a host cell line transfected with the expression vector provided in the present invention.

In the present invention, the "host cell" includes individual cells or cell cultures which may be or have been recipients of the vector(s) for incorporation of a polypeptide insert. The host cell includes progeny of a single host cell, and the progeny may not necessarily be completely identical (in morphology or in genomic DNA complement) to the original parent cell due to natural, accidental, or intentional mutation. The host cell includes cells transfected in vivo with the polynucleotide(s) herein.

In the present invention, the host cell may include cells of mammalian, plant, insect, fungal, or cellular origin, and may be, for example, bacterial cells such as *E. coli, Streptomyces, Salmonella typhimurium*; fungal cells such as yeast cells and *Pichia pastoris*; insect cells such as *Drosophila* and *Spodoptera* Sf9 cells; animal cells such as Chinese hamster ovary (CHO) cells, SP2/0 (mouse myeloma), human lymphoblastoid, COS, NSO (mouse myeloma), 293T, Bowes melanoma cells, HT-1080, baby hamster kidney (BHK) cells, human embryonic kidney (HEK) cells, or PERC.6 (human retinal cells); or plant cells. However, the host cell is not limited thereto, and any cell known to those skilled in the art which can be used as a host cell line is available.

According to still yet another embodiment of the present invention, there is provided an antibody-drug conjugate (ADC) comprising the antibody provided in the present invention and a drug.

As used herein, the term "antibody-drug conjugate (ADC)" refers to a form in which the drug and the antibody are chemically linked to each other without degrading biological activity of the antibody and the drug. In the present invention, the antibody-drug conjugate denotes a form in which the drug is bound to an amino acid residue at the N-terminus of the heavy and/or light chain of the antibody, specifically, a form in which the drug is bound to an α-amine group at the N-terminus of the heavy and/or light chain of the antibody.

As used herein, the term "drug" may mean any substance having a certain biological activity for a cell, which is a concept including DNA, RNA, or a peptide. The drug may be in a form which contains a reactive group capable of reacting and crosslinking with an α-amine group, and also includes a form which contains a reactive group capable of reacting and crosslinking with an α-amine group and to which a linker is linked.

In the present invention, examples of the reactive group capable of reacting and crosslinking with the α-amine group are not particularly limited in terms of type as long as the reactive group can react and crosslink with an α-amine group at the N-terminus of a heavy or light chain of an antibody. The reactive group includes all types of groups known in the art which react with an amine group. The reactive group may, for example, be any one of isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester, but is not limited thereto.

In the present invention, the drug includes any drug regardless of type as long as the drug can treat diseases targeted by the Lrig-1 antibody, and may preferably be a therapeutic agent for immune-related diseases, for example, autoimmune disease, graft versus host disease, organ transplant rejection, asthma, atopy, acute or chronic inflammatory disease, or the like.

According to still yet another embodiment of the present invention, there is provided a pharmaceutical composition for preventing or treating immune-related diseases, comprising, as an active ingredient, the binding molecule or antibody-drug conjugate (ADC) provided in the present invention.

The binding molecule, preferably the antibody, provided in the present invention may activate the function, particularly of regulatory T immune cells (Treg cells), among immune cells; increase the number of the Treg cells; and regulate immunological tolerance, thereby effectively preventing, ameliorating, or treating immune-related diseases.

In the present invention, the "immune-related disease" may be a disease induced by excessive activation and expression of various immune cells and inflammatory cells. The immune-related disease may, for example, include autoimmune disease; graft-versus-host disease; organ transplant rejection; asthma; atopy; or acute or chronic inflammatory disease, but is not limited thereto.

In addition, in the present invention, the "autoimmune disease" may be, but is not limited to, one or more selected from the group consisting of rheumatoid arthritis, systemic scleroderma, systemic lupus erythematosus, atopic dermatitis, psoriasis, alopecia areata, asthma, Crohn's disease, Behcet's disease, Sjogren's syndrome, Guillain-Barré syndrome, chronic thyroiditis, multiple sclerosis, multiple myositis, ankylosing spondylitis, fibrositis, and polyarteritis nodosa.

Meanwhile, in the present invention, the "prevention" may include, without limitation, any act of blocking symptoms of a disease, or suppressing or delaying the symptoms, using the pharmaceutical composition of the present invention.

In addition, in the present invention, the "treatment" may include, without limitation, any act of ameliorating or beneficially altering symptoms of a disease, using the pharmaceutical composition of the present invention.

In the present invention, the pharmaceutical composition may be characterized by being in the form of capsules, tablets, granules, injections, ointments, powders, or beverages, and the pharmaceutical composition may be characterized by being targeted to humans.

In the present invention, the pharmaceutical composition may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition of the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

In the present invention, the "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 50 mg/kg or 0.001 to 50 mg/kg, per day. Administration may be made once a day or several times a day. The dose is not intended to limit the scope of the invention in any way. The pharmaceutical composition according to the present invention may be formulated in the form of pills, sugar-coated tablets, capsules, liquids, gels, syrups, slurries, or suspensions.

Advantageous Effects of Invention

The binding molecule, preferably the antibody, specific for the Lrig-1 protein according to the present invention may activate the function, particularly of regulatory T immune cells (Treg cells), among immune cells; increase the number of the Treg cells; and regulate immunological tolerance, thereby effectively preventing, ameliorating, or treating immune-related diseases, such as autoimmune disease, graft-versus-host diseases, organ transplant rejection, asthma, atopy, or acute or chronic inflammatory disease, which are induced by excessive activation and expression of various immune cells and inflammatory cells.

In addition, the binding molecule, preferably the antibody, specific for the Lrig-1 protein according to the present invention has advantages that the binding molecule is capable of more effectively targeting the Lrig-1 protein as compared with antibodies against Lrig-1 which are previously commercially available, and also has very good binding capacity thereto.

BRIEF DESCRIPTION OF DRAWINGS

FIG. 1 illustrates a structure of the Lrig-1 protein according to an embodiment of the present invention.

FIG. 2 illustrates a structure of the Lrig-1 protein according to an embodiment of the present invention.

FIG. 3 illustrates prediction results for epitopes of the Lrig-1 protein according to an embodiment of the present invention.

FIG. 4 illustrates prediction results for epitopes of the Lrig-1 protein according to an embodiment of the present invention.

FIG. 5 illustrates an expression level of Lrig-1 mRNA according to an embodiment of the present invention.

FIG. 6 illustrates an expression level of Lrig-1 mRNA according to an embodiment of the present invention.

FIG. 7 illustrates an expression level of Lrig-1 mRNA according to an embodiment of the present invention.

FIG. 8 illustrates expression levels of Lrig-1, Lrig-2, and Lrig-3 mRNAs according to an embodiment of the present invention.

FIG. 9 illustrates results obtained by comparing expression levels of Lrig-1 protein in regulatory T cells and non-regulated T cells according to an embodiment of the present invention.

FIG. 10 illustrates expression of the Lrig-1 protein on the surface of regulatory T cells according to an embodiment of the present invention.

FIG. 11 illustrates results obtained by analyzing binding capacity of Lrig-1 protein-specific monoclonal antibodies (A7, C8, E7, and G3) to the Lrig-1 protein according to an embodiment of the present invention.

FIG. 12 illustrates results obtained by analyzing the mechanism of regulating Lrig-1 protein-induced Stat3 phosphorylation, in regulatory T cells, of Lrig-1 protein-specific monoclonal antibodies (A7, C8, E7, and G3) according to an embodiment of the present invention.

FIG. 13 illustrates results obtained by analyzing therapeutic effects, on autoimmune disease, of Lrig-1 protein-specific monoclonal antibodies (A7, C8, E7, and G3) according to an embodiment of the present invention.

DETAILED DESCRIPTION OF INVENTION

According to an embodiment of the present invention, there is provided a binding molecule selected from the group consisting of the following (1) to (4):

(1) a binding molecule comprising a heavy chain variable region that contains a heavy chain CDR1 represented by SEQ ID NO: 5, a heavy chain CDR2 represented by SEQ ID NO: 6, and a heavy chain CDR3 represented by SEQ ID NO: 7; and a light chain variable region that contains a light chain CDR1 represented by SEQ ID NO: 8, a light chain CDR2 represented by SEQ ID NO: 9, and a light chain CDR3 represented by SEQ ID NO: 10;

(2) a binding molecule comprising a heavy chain variable region that contains a heavy chain CDR1 represented by SEQ ID NO: 13, a heavy chain CDR2 represented by SEQ ID NO: 14, and a heavy chain CDR3 represented by SEQ ID NO: 15; and a light chain variable region that contains a light chain CDR1 represented by SEQ ID NO: 16, a light chain CDR2 represented by SEQ ID NO: 17, and a light chain CDR3 represented by SEQ ID NO: 18;

(3) a binding molecule comprising a heavy chain variable region that contains a heavy chain CDR1 represented by SEQ ID NO: 21, a heavy chain CDR2 represented by SEQ ID NO: 22, and a heavy chain CDR3 represented by SEQ ID NO: 23; and a light chain variable region that contains a light chain CDR1 represented by SEQ ID NO: 24, a light chain CDR2 represented by SEQ ID NO: 25, and a light chain CDR3 represented by SEQ ID NO: 26;

(4) a binding molecule comprising a heavy chain variable region that contains a heavy chain CDR1 represented by SEQ ID NO: 29, a heavy chain CDR2 represented by SEQ ID NO: 30, and a heavy chain CDR3 represented by SEQ ID NO: 31; and a light chain variable region that contains a light chain CDR1 represented by SEQ ID NO: 32, a light chain CDR2 represented by SEQ ID NO: 33, and a light chain CDR3 represented by SEQ ID NO: 34.

Hereinafter, the present invention will be described in more detail by way of examples. These examples are only for describing the present invention in more detail, and it will be apparent to those skilled in the art that according to the gist of the present invention, the scope of the present invention is not limited by these examples.

EXAMPLES

[Preparation Example 1] T Cell Subset Cell Culture

In order to identify whether the Lrig-1 protein is expressed only in regulatory T cells (Treg), the subsets of T cells, Th0, Th1, Th2, Th17, and iTreg, were prepared. The iTreg refers to cells whose differentiation has been artificially induced in a medium containing the following composition, unlike nTreg which has been naturally isolated.

The subsets of the T cells were induced to differentiate into respective cells by first isolating naive T cells obtained from the spleen of mice, causing RPMI1640 (Invitrogen Gibco, Grand Island, N.Y.) nutrient medium that contains 10% fetal bovine serum (FBS; HyClone, Logan, Utah) to further contain the respective ingredients of Table 1 below, and performing 72-hour incubation in an incubator at 37° C., 5% $CO_2$.

TABLE 1

| Differentiated cell | Composition |
|---|---|
| Th0 | anti-CD3, anti-CD28 |
| Th1 | IL-12, anti-IL-4 antibody |
| Th2 | IL-4, anti-IFNβ |
| Th17 | IL-6, TGFβ, anti-IFNβ, anti-IL-4 |
| iTreg | IL-2, TGFβ |

[Example 1] Structural Analysis of Lrig-1

A three-dimensional steric structure of the extracellular domain of the Lrig-1 protein was predicted to produce antibodies specific for the Lrig-1 protein, a surface protein of regulatory T cells.

First, in order to predict base sequences of epitopes (epitopes), tools of Uniprot (www.uniprot.org) and RCSB Protein Data Bank (www.rcsb.org/pdb) were used to predict a three-dimensional steric structure of the extracellular domain (ECD) of the Lrig-1 protein so that the structure of ECD is identified. Then, the results are illustrated in FIGS. 1 and 2.

As illustrated in FIG. 1, a total of 15 leucine-rich regions of LRR1 to LRR15 existed in the Lrig-LRR domain (amino acid sequence at positions 41 to 494) in the extracellular domain of the Lrig-1 protein. Each of the LRR domains is composed of 23 to 27 amino acids, with 3 to 5 leucine being present.

In addition, as illustrated in FIG. 2, three immunoglobulin-like domains exist in amino acid sequences at positions 494 to 781 of the Lrig-1 protein in the extracellular domain of the Lrig-1 protein.

[Example 2] Prediction of Lrig-1 Epitope Amino Acid Sequence

Prediction of the above base sequence was performed using Ellipro server (tools.iedb.org/ellipro/) which is an epitope prediction software based on a structure of the Lrig-1 protein. The Ellipro search engine was used because it corresponds to a search engine known to be the most reliable among the existing algorithms for predicting an epitope.

The extracellular domain analyzed in Example 1 was entered into the epitope prediction software, and then predicted contiguous or discontiguous amino acid sequences of the predicted epitopes are illustrated in FIGS. 3 and 4.

As illustrated in FIGS. 3 and 4, a total of 22 contiguous epitope amino acid sequences were predicted, and a total of 8 discontiguous epitope amino acid sequences were predicted.

[Production Examples 1 to 4] Production of Monoclonal Antibodies Specific to Lrig-1 Protein Antibodies specific for the Lrig-1 protein according to the present invention were produced. The present antibodies were not produced by specifying a certain epitope, but were produced as antibodies capable of binding to any site on the Lrig-1 protein.

In order to produce the antibodies, cells expressing the Lrig-1 protein were produced. More specifically, a DNA fragment corresponding to SEQ ID NO: 2 and pcDNA (hygro) were cleaved with a cleavage enzyme, incubated at 37° C., and ligated to produce pcDNA into which a DNA sequence of the Lrig-1 protein is inserted. The thus produced pcDNA into which SEQ ID NO: 2 is inserted was introduced, through transfection, into L cells, so that the Lrig-1 protein is allowed to be expressed on the surface of the L cells.

Light and heavy chain amino acid sequences capable of binding to Lrig-1 expressed on the cell surface were selected from the Human scFv library so that a total of eight heavy and light chains were selected.

The selected heavy and light chain amino acid sequences were fused with the mIgG2a Fc region, to produce monoclonal antibodies. The sequences of the monoclonal antibodies are shown in Table 2 below.

TABLE 2

| Classification | Clone | Location | Amino acid sequence | Sequence information |
|---|---|---|---|---|
| Production Example 1 | A7 clone | Heavy chain | METDTLLLWVLLLWVPGSTWEVQLLESGG GLVQPGGSLRLSCAASGFTFSGYDMSWVRQ APGKGLEWVSLIYPDSGNKYYADSVKGRFTI SRDNSKNTLYLQMNSLRAEDTAVYYCARDA GLSWAGAFDYWGQGTLVTVSSTTAPSVYPL APVCGDTTGSSVTLGCLVKGYFPEPVTLTW NSGSLSSGVHTFPAVLQSDLYTLSSSVTVTSS TWPSQSITCNVAHPASSTKVDKKIEPRGPTIK | SEQ ID NO: 45 |

TABLE 2-continued

| Classification | Clone | Location | Amino acid sequence | Sequence information |
|---|---|---|---|---|
| | | | PCPPCKCPAPNLLGGPSVFIFPPKIKDVLMISL SPIVTCVVVDVSEDDPDVQISWFVNNVEVH TAQTQTHREDYNSTLRVVSALPIQHQDWMS GKEFKCKVNNKDLPAPIERTISKPKGSVRAP QVYVLPPPEEEMTKKQVTLTCMVTDFMPED IYVEWTNNGKTELNYKNTEPVLDSDGSYFM YSKLRVEKKNWVERNSYSCSVVHEGLHNH HTTKSFSRTPGK | |
| | | Light chain | METDTLLLWVLLLWVPGSTWQSVLTQPPSA SGTPGQRVTISCSGSSSNIGSNYVTWYQQLP GTAPKLLIYSDSHRPSGVPDRFSGSKSGTSAS LAISGLQSEDEADYYCGSWDYSLSAYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 46 |
| Production Example 2 | C8 clone | Heavy chain | METDTLLLWVLLLWVPGSTWEVQLLESGG GLVQPGGSLRLSCAASGFTFSNYYMSWVRQ APGKGLEWVSGISPGDSSTYYADSVKGRFTI SRDNSKNTLYLQMNSLRAEDTAVYYCAKGL YSNPNEPFDYWGQGTLVTVSSTTAPSVYPLA PVCGDTTGSSVTLGCLVKGYFPEPVTLTWNS GSLSSGVHTFPAVLQSDLYTLSSSVTVTSSTW PSQSITCNVAHPASSTKVDKKIEPRGPTIKPCP PCKCPAPNLLGGPSVFIFPPKIKDVLMISLSPI VTCVVVDVSEDDPDVQISWFVNNVEVHTAQ TQTHREDYNSTLRVVSALPIQHQDWMSGKE FKCKVNNKDLPAPIERTISKPKGSVRAPQVY VLPPPEEEMTKKQVTLTCMVTDFMPEDIYV EWTNNGKTELNYKNTEPVLDSDGSYFMYS KLRVEKKNWVERNSYSCSVVHEGLHNHHT TKSFSRTPGK | SEQ ID NO: 47 |
| | | Light chain | METDTLLLWVLLLWVPGSTWQSVLTQPPSA SGTPGQRVTISCTGSSSNIGSNYVSWYQQLP GTAPKLLIYDDSQRPSGVPDRFSGSKSGTSA SLAISGLRSEDEADYYCGTWDYSLNGYVFG GGTKLTVLRTVAAPTVSIFPPSSEQLTSGGAS VVCFLNNFYPKDINVKWKIDGSERQNGVLN SWTDQDSKDSTYSMSSTLTLTKDEYERHNS YTCEATHKTSTSPIVKSFNRNEC | SEQ ID NO: 48 |
| Production Example 3 | E7 clone | Heavy chain | METDTLLLWVLLLWVPGSTWEVQLLESGG GLVQPGGSLRLSCAASGFTFSSYDMSWVRQ APGKGLEWVSGISPDGSNIYYADSVKGRFTI SRDNSKNTLYLQMNSLRAEDTAVYYCAKVG LRCRYEACSYAYGMDVWGQGTLVTVSSTTA PSVYPLAPVCGDTTGSSVTLGCLVKGYFPEP VTLTWNSGSLSSGVHTFPAVLQSDLYTLSSS VTVTSSTWPSQSITCNVAHPASSTKVDKKIEP RGPTIKPCPPCKCPAPNLLGGPSVFIFPPKIKD VLMISLSPIVTCVVVDVSEDDPDVQISWFVN NVEVHTAQTQTHREDYNSTLRVVSALPIQH QDWMSGKEFKCKVNNKDLPAPIERTISKPK GSVRAPQVYVLPPPEEEMTKKQVTLTCMVT DFMPEDIYVEWTNNGKTELNYKNTEPVLDS DGSYFMYSKLRVEKKNWVERNSYSCSVVH EGLHNHHTTKSFSRTPGK | SEQ ID NO: 49 |
| | | Light chain | METDTLLLWVLLLWVPGSTWQSVLTQPPSA SGTPGQRVTISCSGSSSNIGSNYVSWYQQLP GTAPKLLIYSDSHRPSGVPDRFSGSKSGTSAS LAISGLRSEDEADYYCATWDSSLNGYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 50 |
| Production Example 4 | G3 clone | Heavy chain | METDTLLLWVLLLWVPGSTWEVQLLESGG GLVQPGGSLRLSCAASGFTFSNYDMSWVRQ APGKGLEWVSSISPSSGSIYYADSVKGRFTIS RDNSKNTLYLQMNSLRAEDTAVYYCAKDLD AFWRPSFDYWGQGTLVTVSSTTAPSVYPLA PVCGDTTGSSVTLGCLVKGYFPEPVTLTWNS GSLSSGVHTFPAVLQSDLYTLSSSVTVTSSTW PSQSITCNVAHPASSTKVDKKIEPRGPTIKPCP PCKCPAPNLLGGPSVFIFPPKIKDVLMISLSPI VTCVVVDVSEDDPDVQISWFVNNVEVHTAQ | SEQ ID NO: 51 |

TABLE 2-continued

| Classification | Clone | Location | Amino acid sequence | Sequence information |
|---|---|---|---|---|
| | | | TQTHREDYNSTLRVVSALPIQHQDWMSGKE FKCKVNNKDLPAPIERTISKPKGSVRAPQVY VLPPPEEEMTKKQVTLTCMVTDFMPEDIYV EWTNNGKTELNYKNTEPVLDSDGSYFMYS KLRVEKKNWVERNSYSCSVVHEGLHNHHT TKSFSRTPGK | |
| | | Light chain | METDTLLLWVLLLWVPGSTWQSVLTQPPSA SGTPGQRVTISCTGSSSNIGNNNVNWYQQLP GTAPKLLIYSDSHRPSGVPDRFSGSKSGTSAS LAISGLRSEDEADYYCGSWDDSLSAYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 52 |
| Production Example 5 | A8 clone | Heavy chain | METDTLLLWVLLLWVPGSTWEVQLLESGG GLVQPGGSLRLSCAASGFTFSDYDMSWVRQ VPGKGLEWVSWISHGGGSIYYADSVKGRFTI SRDNSKNTLYLQMNSLRAEDTAVYYCARGL GLCKTGLCYYYDAMDVWGQGTLVTVSSTT APSVYPLAPVCGDTTGSSVTLGCLVKGYFPE PVTLTWNSGSLSSGVHTFPAVLQSDLYTLSSS VTVTSSTWPSQSITCNVAHPASSTKVDKKIEP RGPTIKPCPPCKCPAPNLLGGPSVFIFPPKIKD VLMISLSPIVTCVVVDVSEDDPDVQISWFVN NVEVHTAQTQTHREDYNSTLRVVSALPIQH QDWMSGKEFKCKVNNKDLPAPIERTISKPK GSVRAPQVYVLPPPEEEMTKKQVTLTCMVT DFMPEDIYVEWTNNGKTELNYKNTEPVLDS DGSYFMYSKLRVEKKNWVERNSYSCSVVH EGLHNHHTTKSFSRTPGK | — |
| | | Light chain | METDTLLLWVLLLWVPGSTWQSVLTQPPSA SGTPGQRVTISCTGSSSNIGNNSVTWYQQLP GTAPKLLIYADNNRPSGVPDRFSGSKSGTSA SLAISGLRSEDEADYYCAAWDSSLSAYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | — |
| Production Example 6 | B8 | Heavy chain | METDTLLLWVLLLWVPGSTWEVQLLESGG GLVQPGGSLRLSCAASGFTFSDYYMSWVRQ APGKGLEWVSGISHDSGSKYYADSVKGRFTI SRDNSKNTLYLQMNSLRAEDTAVYYCARH WTTFDYWGQGTLVTVSSTTAPSVYPLAPVC GDTTGSSVTLGCLVKGYFPEPVTLTWNSGSL SSGVHTFPAVLQSDLYTLSSSVTVTSSTWPSQ SITCNVAHPASSTKVDKKIEPRGPTIKPCPPC KCPAPNLLGGPSVFIFPPKIKDVLMISLSPIVT CVVVDVSEDDPDVQISWFVNNVEVHTAQTQ THREDYNSTLRVVSALPIQHQDWMSGKEFK CKVNNKDLPAPIERTISKPKGSVRAPQVYVL PPPEEEMTKKQVTLTCMVTDFMPEDIYVEW TNNGKTELNYKNTEPVLDSDGSYFMYSKLR VEKKNWVERNSYSCSVVHEGLHNHHTTKS FSRTPGK | — |
| | | Light chain | METDTLLLWVLLLWVPGSTWQSVLTQPPSA SGTPGQRVTISCSGSSSNIGSNNVTWYQQLP GTAPKLLIYANSNRPSGVPDRFSGSKSGTSAS LAISGLRSEDEADYYCGAWDYSLSAYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | — |
| Production Example 7 | D9 clone | Heavy chain | METDTLLLWVLLLWVPGSTWEVQLLESGG GLVQPGGSLRLSCAASGFTFSNYAMSWVRQ APGKGLEWVSAIYPGGGSIYYADSVKGRFTI SRDNSKNTLYLQMNSLRAEDTAVYYCARDI LPCPWGRCYYDYAMDVWGQGTLVTVSSTT APSVYPLAPVCGDTTGSSVTLGCLVKGYFPE PVTLTWNSGSLSSGVHTFPAVLQSDLYTLSSS VTVTSSTWPSQSITCNVAHPASSTKVDKKIEP RGPTIKPCPPCKCPAPNLLGGPSVFIFPPKIKD VLMISLSPIVTCVVVDVSEDDPDVQISWFVN NVEVHTAQTQTHREDYNSTLRVVSALPIQH QDWMSGKEFKCKVNNKDLPAPIERTISKPK | — |

TABLE 2-continued

| Classification | Clone | Location | Amino acid sequence | Sequence information |
|---|---|---|---|---|
| | | | GSVRAPQVYVLPPPEEEMTKKQVTLTCMVT DFMPEDIYVEWTNNGKTELNYKNTEPVLDS DGSYFMYSKLRVEKKNWVERNSYSCSVVH EGLHNHHTTKSFSRTPGK | |
| | | Light chain | METDTLLLWVLLLWVPGSTWQSVLTQPPSA SGTPGQRVTISCSDSSSNIGSNTVSWYQQLP GTAPKLLIYADNNRPSGVPDRFSGSKSGTSA SLAISGLRSEDEADYYCGTWDYSLSGYVFG GGTKLTVLRTVAAPTVSIFPPSSEQLTSGGAS VVCFLNNFYPKDINVKWKIDGSERQNGVLN SWTDQDSKDSTYSMSSTLTLTKDEYERHNS YTCEATHKTSTSPIVKSFNRNEC | — |
| Production Example 8 | H6 clone | Heavy chain | METDTLLLWVLLLWVPGSTWEVQLLESGG GLVQPGGSLRLSCAASGFTFSNYAMSWVRQ APGKGLEWVSVISHGGGSTYYADSVKGRFTI SRDNSKNTLYLQMNSLRAEDTAVYYCARVIS NCHLGVCYYSNGMDVWGQGTLVTVSSTTA PSVYPLAPVCGDTTGSSVTLGCLVKGYFPEP VTLTWNSGSLSSGVHTFPAVLQSDLYTLSSS VTVTSSTWPSQSITCNVAHPASSTKVDKKIEP RGPTIKPCPPCKCPAPNLLGGPSVFIFPPKIKD VLMISLSPIVTCVVVDVSEDDPDVQISWFVN NVEVHTAQTQTHREDYNSTLRVVSALPIQH QDWMSGKEFKCKVNNKDLPAPIERTISKPK GSVRAPQVYVLPPPEEEMTKKQVTLTCMVT DFMPEDIYVEWTNNGKTELNYKNTEPVLDS DGSYFMYSKLRVEKKNWVERNSYSCSVVH EGLHNHHTTKSFSRTPGK | — |
| | | Light chain | METDTLLLWVLLLWVPGSTWQSVLTQPPSA SGTPGQRVTISCSGSSSNIGNNDVYWYQQLP GTAPKLLIYSDSQRPSGVPDRFSGSKSGTSAS LAISGLRSEDEADYYCGTWDYSLSGYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | — |

[Example 3] Identification of Specific Expression of Lrig-1 mRNA in Regulatory T Cells Verification was made of whether the Lrig-1 protein can act as a biomarker specific for regulatory T cells.

For the verification, CD4$^+$ T cells were isolated using magnet-activated cell sorting (MACS), through CD4 beads, from the spleen of mice. Subsequently, regulatory T (CD4$^+$CD25$^+$ T) cells and non-regulatory T (CD4$^+$CD25$^-$ T) cells were isolated with a fluorescence-activated cell sorter (FACS) using a CD25 antibody. For the respective cells and the cells differentiated in Preparation Example 1, mRNA was extracted using Trizol, and gDNA was removed from genomic RNA using gDNA extraction kit (Qiagen) according to the protocol provided by the manufacturer. The gDNA-removed mRNA was synthesized into cDNA through the BDsprint cDNA Synthesis Kit (Clonetech).

Real-time polymerase chain reaction (RT PCR) was performed to quantitatively identify an expression level of Lrig-1 mRNA in the cDNA.

The real-time polymerase chain reaction was performed with primers shown in Table 3 below using SYBR Green (Molecular Probes) by the protocol provided by the manufacturer under conditions of 40 cycles consisting of 95° C. for 3 minutes, 61° C. for 15 seconds, 72° C. for 30 seconds, a relative gene expression level was calculated using the ΔΔCT method, and normalized using HPRT. The results are illustrated in FIGS. 5 to 8.

```
Primer Sequence

Mouse    Forward  5'-GAC GGA ATT CAG TGA GGA GAA CCT-3'
Lrig-1   Reverse  5'-CAA CTG GTA GTG GCA GCT TGT AGG-3'

Mouse    forward  5'-TCA CAA GGA ACA TTG TCT GAA CCA-3'
Lrig-2   reverse  5'-GCC TGA TCT AAC ACA TCC TCC TCA-3'

Mouse    forward  5'-CAG CAC CTT GAG CTG AAC AGA AAC-3'
Lrig-3   reverse  5'-CCA GCC TTT GGT AAT CTC GGT TAG-3'

Mouse    forward  5'-CTT TCA CCT ATC CCA CCC TTA TCC-3'
FOXP3    reverse  5'-ATT CAT CTA CGG TCC ACA CTG CTC-3'

ACTG1    forward  5'-GGC GTC ATG GTG GGC ATG GG-3'
         reverse  5'-ATG GCG TGG GGA AGG GCG TA-3'
```

As illustrated in FIG. 5, it can be seen that the expression of Lrig-1 in regulatory T (CD4$^+$CD25$^+$ T) cells is 18.1 times higher than non-regulatory T (CD4$^+$CD25$^-$ T) cells. This was about 10 times higher expression level than Lag3 and Ikzf4, which are previously known markers for regulatory T cells. In addition, as illustrated in FIGS. 6 and 7, the expression of Lrig-1 mRNA was remarkably high in regulatory T cells as compared with other types of immune cells, and in particular, was remarkably high in naturally isolated regulatory T cells (nTreg) as compared with induced regulatory T cells (iTreg cells).

In addition, as illustrated in FIG. 8, expression of Lrig-1 was the highest among Lrig-1, Lrig-2, and Lrig-3 which correspond to the Lrig family.

From the above results, it can be seen that the Lrig-1 protein according to the present invention is specifically expressed in regulatory T cells, in particular, naturally-occurring regulatory T cells.

[Example 4] Identification of Specific Expression of Lrig-1 Protein in Regulatory T Cells It was identified whether the Lrig-1 protein expressed from Lrig-1 mRNA is specifically expressed only in regulatory T cells.

Using FOXP3-RFP-knocked-in mice, the FOXP3-RFP obtained by coupling red fluorescence protein (RFP) to FOXP3 promoter, a transcription factor specific for regulatory T cells, CD4$^+$ T cells were isolated using magnet-activated cell sorting (MACS), through CD4 beads, from the spleen of the mice. Subsequently, using RFP protein, regulatory T (CD4$^+$RFP$^+$ T) cells and non-regulatory T (CD4$^+$RFP$^-$ T) cells were obtained by performing isolation through a fluorescence-activated cell sorter (FACS). The respective cells were stained with the purchased Lrig-1 antibody and a negative control was stained with an isotype-matched control antibody, to measure an expression level of Lrig-1 with the fluorescence-activated cell sorter. The results are illustrated in FIG. 9.

As illustrated in FIG. 9, the non-regulatory T cells indicated by a dotted line showed almost the same expression level of Lrig-1 as the negative control, whereas there were a large number of cells with high expression level of Lrig-1 in the regulatory T cells.

From the above results, it can be seen that the Lrig-1 protein according to the present invention is specifically expressed in regulatory T cells.

[Example 5] Identification of Specific Expression of Lrig-1 Protein on Surface of Regulatory T Cells From the viewpoint that in order to be a target of cell therapy, the Lrig-1 protein must be expressed on the surface of regulatory T cells, which in turn allows a more effective target therapy, it was identified whether the Lrig-1 protein is expressed on the surface of the regulatory T cells.

The respective differentiated T cell subsets of Preparation Example 1 were stained with anti-CD4-APC and anti-Lrig-1-PE antibodies, and expression levels of Lrig-1 were measured at the respective cell surfaces using a fluorescence-activated cell sorter (FACS). The results are illustrated in FIG. 10.

As illustrated in FIG. 10, Lrig-1 was expressed in an amount of 0.77 to 15.3 in activated T cells, Th1 cells, Th2 cells, Th17 cells, and naive T cells, whereas Lrig-1 was expressed as high as 83.9 in differentiation-induced T cells (iTreg cells).

From the above results, it can be seen that the Lrig-1 protein according to the present invention is not only specifically expressed in regulatory T (Treg) cells, but also is, in particular, expressed at a higher level on the surface of the Treg cells.

[Example 6] Evaluation of Binding Capacity of Antibody According to Present Invention to Lrig-1 Protein In order to identify whether the monoclonal antibodies according to the present invention produced in Production Examples 1 to 8 well recognize Lrig-1, each of the antibodies of Production Examples 1 to 8 was bound to L cells that stably express Lrig-1. Then, a secondary antibody which is conjugated with eFlour 670 and is capable of recognizing the mouse antibodies was added thereto, and then binding capacity of the monoclonal antibodies to the Lrig-1 protein was analyzed using FACS. The results are illustrated in FIG. 11.

As illustrated in FIG. 11, it was found that all Lrig-1 protein-specific monoclonal antibodies (A7, C8, E7, and G3) according to the present invention effectively recognize and bind to the Lrig-1 protein present on the surface of L cells.

[Example 7] Regulation of Signal Transduction Pathway in Treg Cells, by Antibody According to Present Invention In order to analyze how the monoclonal antibodies according to the present invention produced in Production Examples 1 to 8 affect the signal transduction pathway in Treg cells through the Lrig-1 protein, Lrig-1 present on the surface of the Treg cells was stimulated by treating the Treg cells with the antibodies of Production Examples 1 to 8, and then a level of tyrosine phosphorylation of Stat3 protein present in the stimulated Treg cells was analyzed through phosphotyrosine immunoblot. The results are illustrated in FIG. 12.

As illustrated in FIG. 12, it was found that the Lrig-1 protein-specific monoclonal antibodies (A7, C8, E7, and G3) according to the present invention increase phosphorylation of Stat3 to the same level as Th17 cells.

[Example 8] Therapeutic Effects of Antibody According to the Present Invention on Autoimmune Disease In order to identify therapeutic effects of the monoclonal antibodies (A7, C8, E7, and G3) according to the present invention produced in Production Examples 1 to 4 on autoimmune disease, RAG-1$^{-/-}$ mice were subjected to adoptive transfer with CD45RB (high) cells so that inflammatory bowel disease (IBD), which is autoimmune disease, was induced. Then, the antibodies of Production Examples 1 to 4 were intraperitoneally injected in an amount of 200 μg/mouse, and then therapeutic effects thereof on the autoimmune disease were analyzed. The results are illustrated in FIG. 13.

As illustrated in FIG. 13, it was found that the Lrig-1 protein-specific monoclonal antibodies (A7, C8, E7, and G3) according to the present invention remarkably inhibit a body weight-decreasing effect in inflammatory bowel disease-induced mice.

From this, it can be seen that the Lrig-1 protein-specific monoclonal antibody according to the present invention are capable of effectively preventing, ameliorating, or treating immune-related diseases, such as autoimmune disease, graft-versus-host disease, organ transplant rejection, asthma, atopy, or acute or chronic inflammatory disease, which are induced by excessive activation and expression of various immune cells and inflammatory cells.

Although the present invention has been described in detail above, the scope of the present invention is not limited thereto. It will be obvious to those skilled in the art that various modifications and changes can be made without departing from the technical spirit of the present invention described in the claims.

INDUSTRIAL APPLICABILITY

The present invention relates to a binding molecule capable of specifically binding to leucine-rich and immunoglobulin-like domains 1 (Lrig-1) protein, which is a protein present on the surface of regulatory T cells (Treg cells), and a use thereof, specifically, prevention or treatment of immune-related diseases, such as autoimmune disease, graft-versus-host diseases, organ transplant rejection, asthma, atopy, or acute or chronic inflammatory disease.

The invention claimed is:

1. A binding molecule which specifically binds to leucine-rich and immunoglobulin-like domains 1 (Lrig-1) protein, wherein the binding molecule is selected from the group consisting of the following (a) to (d):

(a) a binding molecule comprising a heavy chain variable region that contains the heavy chain CDR1 represented by SEQ ID NO: 5, the heavy chain CDR2 represented by SEQ ID NO: 6, and the heavy chain CDR3 represented by SEQ ID NO: 7; and a light chain variable region that contains the light chain CDR1 represented by SEQ ID NO: 8, the light chain CDR2 represented by SEQ ID NO: 9, and the light chain CDR3 represented by SEQ ID NO: 10;

(b) a binding molecule comprising a heavy chain variable region that contains the heavy chain CDR1 represented by SEQ ID NO: 13, the heavy chain CDR2 represented by SEQ ID NO: 14, and the heavy chain CDR3 represented by SEQ ID NO: 15; and a light chain variable region that contains the light chain CDR1 represented by SEQ ID NO: 16, the light chain CDR2 represented by SEQ ID NO: 17, and the light chain CDR3 represented by SEQ ID NO: 18;

(c) a binding molecule comprising a heavy chain variable region that contains the heavy chain CDR1 represented by SEQ ID NO: 21, the heavy chain CDR2 represented by SEQ ID NO: 22, and the heavy chain CDR3 represented by SEQ ID NO: 23; and the light chain variable region that contains the light chain CDR1 represented by SEQ ID NO: 24, the light chain CDR2 represented by SEQ ID NO: 25, and the light chain CDR3 represented by SEQ ID NO: 26; and (d) a binding molecule comprising a heavy chain variable region that contains the heavy chain CDR1 represented by SEQ ID NO: 29, the heavy chain CDR2 represented by SEQ ID NO: 30, and the heavy chain CDR3 represented by SEQ ID NO: 31; and a light chain variable region that contains the light chain CDR1 represented by SEQ ID NO: 32, the light chain CDR2 represented by SEQ ID NO: 33, and the light chain CDR3 represented by SEQ ID NO: 34.

2. The binding molecule according to claim 1, further comprising:
an Fc region or a constant region.

3. The binding molecule according to claim 2, wherein the Fc region is an Fc region of an IgG1, IgG2, IgG3, or IgG4 antibody, or a hybrid Fc region.

4. The binding molecule according to claim 1, further comprising:
a heavy chain constant region consisting of the amino acid sequence selected from the group consisting of SEQ ID NOs: 37, 39, 41, 42, 43, and 44.

5. The binding molecule according to claim 1, further comprising:
a light chain constant region consisting of the amino acid sequence represented by SEQ ID NO: 38 or 40.

6. The binding molecule according to claim 1, further comprising:
a heavy chain constant region consisting of the amino acid sequence represented by SEQ ID NO: 37; and a light chain constant region consisting of the amino acid sequence represented by SEQ ID NO: 38.

7. The binding molecule according to claim 1, further comprising:
a heavy chain constant region consisting of the amino acid sequence represented by SEQ ID NO: 39, 41, 42, or 43; and
a light chain constant region consisting of the amino acid sequence represented by SEQ ID NO: 40.

8. The binding molecule according to claim 1, further comprising:
a heavy chain constant region consisting of the amino acid sequence represented by SEQ ID NO: 44.

9. The binding molecule according to claim 1, wherein the binding molecule is an antibody or a fragment thereof.

10. The binding molecule according to claim 9, wherein the antibody is a chimeric antibody, a humanized antibody, a bivalent antibody, a minibody, an antibody mimetic, a diabody, a triabody, or a tetrabody, or a fragment thereof.

11. A pharmaceutical composition comprising as an active ingredient:
the binding molecule according to claim 1.

12. A method for treating immune-related diseases, comprising:
a step of administering the binding molecule according to claim 1 to a subject in need of treatment, so as to treat the immune-related disease, wherein the immune-related disease is autoimmune disease, graft versus host disease, organ transplant resection, asthma, atopy, or acute or chronic inflammatory disease.

* * * * *

```
                            SEQUENCE LISTING

<160> NUMBER OF SEQ ID NOS: 52

<210> SEQ ID NO 1
<211> LENGTH: 759
<212> TYPE: PRT
<213> ORGANISM: Homo sapiens

<400> SEQUENCE: 1

Gly Pro Arg Ala Pro Cys Ala Ala Cys Thr Cys Ala Gly Asp Ser
1               5                   10                  15

Leu Asp Cys Gly Gly Arg Gly Leu Ala Ala Leu Pro Gly Asp Leu Pro
                20                  25                  30

Ser Trp Thr Arg Ser Leu Asn Leu Ser Tyr Asn Lys Leu Ser Glu Ile
            35                  40                  45

Asp Pro Ala Gly Phe Glu Asp Leu Pro Asn Leu Gln Glu Val Tyr Leu
        50                  55                  60

Asn Asn Asn Glu Leu Thr Ala Val Pro Ser Leu Gly Ala Ala Ser Ser
65                  70                  75                  80

His Val Val Ser Leu Phe Leu Gln His Asn Lys Ile Arg Ser Val Glu
                85                  90                  95

Gly Ser Gln Leu Lys Ala Tyr Leu Ser Leu Glu Val Leu Asp Leu Ser
                100                 105                 110

Leu Asn Asn Ile Thr Glu Val Arg Asn Thr Cys Phe Pro His Gly Pro
            115                 120                 125

Pro Ile Lys Glu Leu Asn Leu Ala Gly Asn Arg Ile Gly Thr Leu Glu
        130                 135                 140

Leu Gly Ala Phe Asp Gly Leu Ser Arg Ser Leu Leu Thr Leu Arg Leu
145                 150                 155                 160

Ser Lys Asn Arg Ile Thr Gln Leu Pro Val Arg Ala Phe Lys Leu Pro
                165                 170                 175

Arg Leu Thr Gln Leu Asp Leu Asn Arg Asn Arg Ile Arg Leu Ile Glu
                180                 185                 190

Gly Leu Thr Phe Gln Gly Leu Asn Ser Leu Glu Val Leu Lys Leu Gln
            195                 200                 205

Arg Asn Asn Ile Ser Lys Leu Thr Asp Gly Ala Phe Trp Gly Leu Ser
        210                 215                 220

Lys Met His Val Leu His Leu Glu Tyr Asn Ser Leu Val Glu Val Asn
225                 230                 235                 240

Ser Gly Ser Leu Tyr Gly Leu Thr Ala Leu His Gln Leu His Leu Ser
                245                 250                 255

Asn Asn Ser Ile Ala Arg Ile His Arg Lys Gly Trp Ser Phe Cys Gln
                260                 265                 270

Lys Leu His Glu Leu Val Leu Ser Phe Asn Asn Leu Thr Arg Leu Asp
            275                 280                 285

Glu Glu Ser Leu Ala Glu Leu Ser Ser Leu Ser Val Leu Arg Leu Ser
        290                 295                 300

His Asn Ser Ile Ser His Ile Ala Glu Gly Ala Phe Lys Gly Leu Arg
305                 310                 315                 320

Ser Leu Arg Val Leu Asp Leu Asp His Asn Glu Ile Ser Gly Thr Ile
                325                 330                 335

Glu Asp Thr Ser Gly Ala Phe Ser Gly Leu Asp Ser Leu Ser Lys Leu
```

```
                    340                 345                 350
Thr Leu Phe Gly Asn Lys Ile Lys Ser Val Ala Lys Arg Ala Phe Ser
            355                 360                 365

Gly Leu Glu Gly Leu Glu His Leu Asn Leu Gly Gly Asn Ala Ile Arg
        370                 375                 380

Ser Val Gln Phe Asp Ala Phe Val Lys Met Lys Asn Leu Lys Glu Leu
385                 390                 395                 400

His Ile Ser Ser Asp Ser Phe Leu Cys Asp Cys Gln Leu Lys Trp Leu
                405                 410                 415

Pro Pro Trp Leu Ile Gly Arg Met Leu Gln Ala Phe Val Thr Ala Thr
            420                 425                 430

Cys Ala His Pro Glu Ser Leu Lys Gly Gln Ser Ile Phe Ser Val Pro
        435                 440                 445

Pro Glu Ser Phe Val Cys Asp Asp Phe Leu Lys Pro Gln Ile Ile Thr
    450                 455                 460

Gln Pro Glu Thr Thr Met Ala Met Val Gly Lys Asp Ile Arg Phe Thr
465                 470                 475                 480

Cys Ser Ala Ala Ser Ser Ser Ser Pro Met Thr Phe Ala Trp Lys
                485                 490                 495

Lys Asp Asn Glu Val Leu Thr Asn Ala Asp Met Glu Asn Phe Val His
            500                 505                 510

Val His Ala Gln Asp Gly Glu Val Met Glu Tyr Thr Thr Ile Leu His
        515                 520                 525

Leu Arg Gln Val Thr Phe Gly His Glu Gly Arg Tyr Gln Cys Val Ile
    530                 535                 540

Thr Asn His Phe Gly Ser Thr Tyr Ser His Lys Ala Arg Leu Thr Val
545                 550                 555                 560

Asn Val Leu Pro Ser Phe Thr Lys Thr Pro His Asp Ile Thr Ile Arg
                565                 570                 575

Thr Thr Thr Val Ala Arg Leu Glu Cys Ala Ala Thr Gly His Pro Asn
            580                 585                 590

Pro Gln Ile Ala Trp Gln Lys Asp Gly Gly Thr Asp Phe Pro Ala Ala
        595                 600                 605

Arg Glu Arg Arg Met His Val Met Pro Asp Asp Val Phe Phe Ile
    610                 615                 620

Thr Asp Val Lys Ile Asp Asp Ala Gly Val Tyr Ser Cys Thr Ala Gln
625                 630                 635                 640

Asn Ser Ala Gly Ser Ile Ser Ala Asn Ala Thr Leu Thr Val Leu Glu
                645                 650                 655

Thr Pro Ser Leu Val Val Pro Leu Glu Asp Arg Val Val Ser Val Gly
            660                 665                 670

Glu Thr Val Ala Leu Gln Cys Lys Ala Thr Gly Asn Pro Pro Pro Arg
        675                 680                 685

Ile Thr Trp Phe Lys Gly Asp Arg Pro Leu Ser Leu Thr Glu Arg His
    690                 695                 700

His Leu Thr Pro Asp Asn Gln Leu Leu Val Val Gln Asn Val Val Ala
705                 710                 715                 720

Glu Asp Ala Gly Arg Tyr Thr Cys Glu Met Ser Asn Thr Leu Gly Thr
                725                 730                 735

Glu Arg Ala His Ser Gln Leu Ser Val Leu Pro Ala Ala Gly Cys Arg
            740                 745                 750

Lys Asp Gly Thr Thr Val Gly
        755
```

<210> SEQ ID NO 2
<211> LENGTH: 2397
<212> TYPE: DNA
<213> ORGANISM: Homo sapiens

<400> SEQUENCE: 2

| | | | | | |
|---|---|---|---|---|---|
| ggcccgcggg | cgccctgcgc | ggccgcctgc | acttgcgctg | gggactcgct | ggactgcggt | 60 |
| gggcgcgggc | tggctgcgtt | gcccggggac | ctgccctcct | ggacgcggag | cctaaacctg | 120 |
| agttacaaca | aactctctga | gattgaccct | gctggttttg | aggacttgcc | gaacctacag | 180 |
| gaagtgtacc | tcaataataa | tgagttgaca | gcggtaccat | ccctgggcgc | tgcttcatca | 240 |
| catgtcgtct | ctctctttct | gcagcacaac | aagattcgca | gcgtggaggg | gagccagctg | 300 |
| aaggcctacc | tttccttaga | agtgttagat | ctgagtttga | acaacatcac | ggaagtgcgg | 360 |
| aacacctgct | ttccacacgg | accgcctata | aaggagctca | acctggcagg | caatcggatt | 420 |
| ggcaccctgg | agttgggagc | atttgatggt | ctgtcacggt | cgctgctaac | tcttcgcctg | 480 |
| agcaaaaaca | ggatcaccca | gcttcctgta | agagcattca | agctacccag | gctgacacaa | 540 |
| ctggacctca | atcggaacag | gattcggctg | atagagggcc | tcaccttcca | ggggctcaac | 600 |
| agcttggagg | tgctgaagct | tcagcgaaac | aacatcagca | aactgacaga | tggggccttc | 660 |
| tggggactgt | ccaagatgca | tgtgctgcac | ctggagtaca | acagcctggt | agaagtgaac | 720 |
| agcggctcgc | tctacggcct | cacggccctg | catcagctcc | acctcagcaa | caattccatc | 780 |
| gctcgcattc | accgcaaggg | ctggagcttc | tgccagaagc | tgcatgagtt | ggtcctgtcc | 840 |
| ttcaacaacc | tgacacggct | ggacgaggag | agcctggccg | agctgagcag | cctgagtgtc | 900 |
| ctgcgtctca | gccacaattc | catcagccac | attgcggagg | gtgccttcaa | gggactcagg | 960 |
| agcctgcgag | tcttggatct | ggaccataac | gagatttcgg | gcacaataga | ggacacgagc | 1020 |
| ggcgccttct | cagggctcga | cagcctcagc | aagctgactc | tgtttggaaa | caagatcaag | 1080 |
| tctgtggcta | agagagcatt | ctcggggctg | gaaggcctgg | agcacctgaa | ccttggaggg | 1140 |
| aatgcgatca | gatctgtcca | gtttgatgcc | tttgtgaaga | tgaagaatct | taaagagctc | 1200 |
| catatcagca | gcgacagctt | cctgtgtgac | tgccagctga | agtggctgcc | ccgtggcta | 1260 |
| attggcagga | tgctgcaggc | ctttgtgaca | gccacctgtg | cccacccaga | atcactgaag | 1320 |
| ggtcagagca | tttttctctgt | gccaccagag | agtttcgtgt | gcgatgactt | cctgaagcca | 1380 |
| cagatcatca | cccagccaga | aaccaccatg | gctatggtgg | gcaaggacat | ccggtttaca | 1440 |
| tgctcagcag | ccagcagcag | cagctccccc | atgacctttg | cctggaagaa | agacaatgaa | 1500 |
| gtcctgacca | atgcagacat | ggagaacttt | gtccacgtcc | acgcgcagga | cggggaagtg | 1560 |
| atggagtaca | ccaccatcct | gcacctccgt | caggtcactt | tcgggcacga | gggccgctac | 1620 |
| caatgtgtca | tcaccaacca | ctttggctcc | acctattcac | ataaggccag | gctcaccgtg | 1680 |
| aatgtgttgc | catcattcac | caaaacgccc | cacgacataa | ccatccggac | caccaccgtg | 1740 |
| gcccgcctcg | aatgtgctgc | cacaggtcac | ccaaaccctc | agattgcctg | gcagaaggat | 1800 |
| ggaggcacgg | atttccccgc | tgcccgtgag | cgacgcatgc | atgtcatgcc | ggatgacgac | 1860 |
| gtgttttttca | tcactgatgt | gaaaatagat | gacgcagggg | tttacagctg | tactgctcag | 1920 |
| aactcagccg | gttctatttc | agctaatgcc | accctgactg | tcctagagac | cccatccttg | 1980 |
| gtggtccccct | tggaagaccg | tgtggtatct | gtgggagaaa | cagtgccct | caatgcaaa | 2040 |
| gccacgggga | accctccgcc | ccgcatcacc | tggttcaagg | gggaccgccc | gctgagcctc | 2100 |

-continued

```
actgagcggc accacctgac ccctgacaac cagctcctgg tggttcagaa cgtggtggca    2160
gaggatgcgg gccgatatac ctgtgagatg tccaacaccc tgggcacgga gcgagctcac    2220
agccagctga gcgtcctgcc cgcagcaggc tgcaggaagg atgggaccac ggtaggcatc    2280
ttcaccattg ctgtcgtgag cagcatcgtc ctgacgtcac tggtctgggt gtgcatcatc    2340
taccagacca ggaagaagag tgaagagtac agtgtcacca cacagatga aaccgtc       2397
```

<210> SEQ ID NO 3
<211> LENGTH: 761
<212> TYPE: PRT
<213> ORGANISM: Mus musculus

<400> SEQUENCE: 3

```
Gln Ala Gly Pro Arg Ala Pro Cys Ala Ala Cys Thr Cys Ala Gly
1               5                   10                  15

Asp Ser Leu Asp Cys Ser Gly Arg Gly Leu Ala Thr Leu Pro Arg Asp
            20                  25                  30

Leu Pro Ser Trp Thr Arg Ser Leu Asn Leu Ser Tyr Asn Arg Leu Ser
        35                  40                  45

Glu Ile Asp Ser Ala Ala Phe Glu Asp Leu Thr Asn Leu Gln Glu Val
    50                  55                  60

Tyr Leu Asn Ser Asn Glu Leu Thr Ala Ile Pro Ser Leu Gly Ala Ala
65                  70                  75                  80

Ser Ile Gly Val Val Ser Leu Phe Leu Gln His Asn Lys Ile Leu Ser
                85                  90                  95

Val Asp Gly Ser Gln Leu Lys Ser Tyr Leu Ser Leu Glu Val Leu Asp
            100                 105                 110

Leu Ser Ser Asn Asn Ile Thr Glu Ile Arg Ser Ser Cys Phe Pro Asn
        115                 120                 125

Gly Leu Arg Ile Arg Glu Leu Asn Leu Ala Ser Asn Arg Ile Ser Ile
    130                 135                 140

Leu Glu Ser Gly Ala Phe Asp Gly Leu Ser Arg Ser Leu Leu Thr Leu
145                 150                 155                 160

Arg Leu Ser Lys Asn Arg Ile Thr Gln Leu Pro Val Lys Ala Phe Lys
                165                 170                 175

Leu Pro Arg Leu Thr Gln Leu Asp Leu Asn Arg Asn Arg Ile Arg Leu
            180                 185                 190

Ile Glu Gly Leu Thr Phe Gln Gly Leu Asp Ser Leu Glu Val Leu Arg
        195                 200                 205

Leu Gln Arg Asn Asn Ile Ser Arg Leu Thr Asp Gly Ala Phe Trp Gly
    210                 215                 220

Leu Ser Lys Met His Val Leu His Leu Glu Tyr Asn Ser Leu Val Glu
225                 230                 235                 240

Val Asn Ser Gly Ser Leu Tyr Gly Leu Thr Ala Leu His Gln Leu His
                245                 250                 255

Leu Ser Asn Asn Ser Ile Ser Arg Ile Gln Arg Asp Gly Trp Ser Phe
            260                 265                 270

Cys Gln Lys Leu His Glu Leu Ile Leu Ser Phe Asn Asn Leu Thr Arg
        275                 280                 285

Leu Asp Glu Glu Ser Leu Ala Glu Leu Ser Ser Leu Ser Ile Leu Arg
    290                 295                 300

Leu Ser His Asn Ala Ile Ser His Ile Ala Glu Gly Ala Phe Lys Gly
305                 310                 315                 320

Leu Lys Ser Leu Arg Val Leu Asp Leu Asp His Asn Glu Ile Ser Gly
```

```
                325                 330                 335
Thr Ile Glu Asp Thr Ser Gly Ala Phe Thr Gly Leu Asp Asn Leu Ser
            340                 345                 350
Lys Leu Thr Leu Phe Gly Asn Lys Ile Lys Ser Val Ala Lys Arg Ala
            355                 360                 365
Phe Ser Gly Leu Glu Ser Leu Glu His Leu Asn Leu Gly Glu Asn Ala
            370                 375                 380
Ile Arg Ser Val Gln Phe Asp Ala Phe Ala Lys Met Lys Asn Leu Lys
385                 390                 395                 400
Glu Leu Tyr Ile Ser Ser Glu Ser Phe Leu Cys Asp Cys Gln Leu Lys
            405                 410                 415
Trp Leu Pro Pro Trp Leu Met Gly Arg Met Leu Gln Ala Phe Val Thr
            420                 425                 430
Ala Thr Cys Ala His Pro Glu Ser Leu Lys Gly Gln Ser Ile Phe Ser
            435                 440                 445
Val Leu Pro Asp Ser Phe Val Cys Asp Asp Phe Pro Lys Pro Gln Ile
            450                 455                 460
Ile Thr Gln Pro Glu Thr Thr Met Ala Val Val Gly Lys Asp Ile Arg
465                 470                 475                 480
Phe Thr Cys Ser Ala Ala Ser Ser Ser Ser Pro Met Thr Phe Ala
                    485                 490                 495
Trp Lys Lys Asp Asn Glu Val Leu Ala Asn Ala Asp Met Glu Asn Phe
            500                 505                 510
Ala His Val Arg Ala Gln Asp Gly Glu Val Met Glu Tyr Thr Thr Ile
            515                 520                 525
Leu His Leu Arg His Val Thr Phe Gly His Glu Gly Arg Tyr Gln Cys
            530                 535                 540
Ile Ile Thr Asn His Phe Gly Ser Thr Tyr Ser His Lys Ala Arg Leu
545                 550                 555                 560
Thr Val Asn Val Leu Pro Ser Phe Thr Lys Ile Pro His Asp Ile Ala
                    565                 570                 575
Ile Arg Thr Gly Thr Thr Ala Arg Leu Glu Cys Ala Ala Thr Gly His
            580                 585                 590
Pro Asn Pro Gln Ile Ala Trp Gln Lys Asp Gly Gly Thr Asp Phe Pro
            595                 600                 605
Ala Ala Arg Glu Arg Arg Met His Val Met Pro Asp Asp Val Phe
            610                 615                 620
Phe Ile Thr Asp Val Lys Ile Asp Asp Met Gly Val Tyr Ser Cys Thr
625                 630                 635                 640
Ala Gln Asn Ser Ala Gly Ser Val Ser Ala Asn Ala Thr Leu Thr Val
                    645                 650                 655
Leu Glu Thr Pro Ser Leu Ala Val Pro Leu Glu Asp Arg Val Val Thr
            660                 665                 670
Val Gly Glu Thr Val Ala Phe Gln Cys Lys Ala Thr Gly Ser Pro Thr
            675                 680                 685
Pro Arg Ile Thr Trp Leu Lys Gly Gly Arg Pro Leu Ser Leu Thr Glu
            690                 695                 700
Arg His His Phe Thr Pro Gly Asn Gln Leu Leu Val Val Gln Asn Val
705                 710                 715                 720
Met Ile Asp Asp Ala Gly Arg Tyr Thr Cys Glu Met Ser Asn Pro Leu
                    725                 730                 735
Gly Thr Glu Arg Ala His Ser Gln Leu Ser Ile Leu Pro Thr Pro Gly
            740                 745                 750
```

Cys Arg Lys Asp Gly Thr Thr Val Gly
        755                 760

<210> SEQ ID NO 4
<211> LENGTH: 2283
<212> TYPE: DNA
<213> ORGANISM: Mus musculus

<400> SEQUENCE: 4

| | | | | | |
|---|---|---|---|---|---|
| caggctggcc | cgcgggcccc | ctgcgcggcc | gcctgcactt | gcgccgggga | ctcgctggac | 60 |
| tgcagtgggc | gcgggctggc | gacgctgccc | cgggacctgc | cctcctggac | gcgcagccta | 120 |
| aacctgagtt | ataacagact | ctccgagatc | gactctgctg | cttttgagga | cttgacgaat | 180 |
| ctgcaggaag | tgtacctcaa | cagcaatgag | ctgacagcca | taccatcact | gggcgctgct | 240 |
| tccataggag | ttgtctctct | cttttttgcag | cacaacaaga | tccttagtgt | ggatgggagc | 300 |
| cagctgaagt | cgtacctgtc | cttggaagtg | ctggatctga | gttccaacaa | catcacggaa | 360 |
| attcggagct | cctgtttccc | gaacggcctg | cgtataaggg | aactcaactt | ggcgagcaac | 420 |
| cgcatcagca | tcctggagtc | tggagcattt | gatggtctgt | cgcggtcact | gctgactctc | 480 |
| cgtctgagca | aaaacaggat | cacccagctt | cctgtgaaag | cgttcaagct | acccaggctg | 540 |
| acacaactag | acctgaatcg | gaatcggatt | cggctgattg | aaggcctcac | gttccagggg | 600 |
| ctcgacagct | tagaggtgct | gaggcttcag | aggaacaaca | tcagcaggct | gacggacggg | 660 |
| gccttctggg | ggctgtctaa | gatgcacgtg | ctgcacctgg | agtacaacag | tctggtggaa | 720 |
| gtgaacagtg | gctccctcta | tggcctcaca | gccctgcacc | agctgcacct | cagcaacaac | 780 |
| tccatctctc | gaattcagcg | tgatggctgg | agcttctgcc | aaaagctgca | tgagttgatt | 840 |
| ctgtccttca | caaccctcac | gcggctggat | gaggagagtc | tagcggagtt | gagcagcctc | 900 |
| agtatcctgc | gcctcagtca | aacgccatc | agtcacattg | ctgaaggcgc | cttcaaggga | 960 |
| ctcaagagtc | tgcgggtctt | ggacctgac | cataacgaga | tctcgggtac | aatcgaggat | 1020 |
| accagtggtg | cctttacggg | gcttgacaac | ctcagcaagc | tgactctgtt | tggaaacaag | 1080 |
| atcaaatctg | tggctaagag | agccttctcg | ggcctggaaa | gcctggaaca | cctgaacctt | 1140 |
| ggagagaatg | caatcaggtc | tgtccagttt | gatgcctttg | caaagatgaa | gaaccttaaa | 1200 |
| gagctctaca | tcagcagtga | gagcttcctg | tgtgactgcc | agctcaagtg | gctgccccca | 1260 |
| tggctaatgg | gtaggatgct | gcaggccttt | gtgacagcca | cctgtgccca | tccagagtcg | 1320 |
| ctgaagggcc | agagcatttt | ctcagtgctg | ccagacagct | ttgtgtgtga | tgactttcca | 1380 |
| aagccacaga | tcatcaccca | gcctgagacg | accatggctg | tggtgggcaa | ggacatccgt | 1440 |
| ttcacatgct | ccgcagccag | cagcagcagc | tcaccaatga | ccttcgcctg | gaagaaggac | 1500 |
| aatgaggtcc | tggccaatgc | agacatggag | aactttgccc | acgtccgtgc | acaggacggc | 1560 |
| gaagtgatgg | agtataccac | tatcctgcac | ctccgtcacg | tcacctttgg | gcacgagggc | 1620 |
| cgctaccagt | gtatcatcac | aaaccacttt | ggctccacat | actcccacaa | agccaggctc | 1680 |
| actgtgaatg | tgttgccatc | attcactaaa | ataccccatg | acattgccat | ccggactggc | 1740 |
| accacagccc | gcctcgagtg | tgctgccacg | ggccaccctt | accctcagat | tgcctggcag | 1800 |
| aaggatggag | gcaccgattt | cccggcagct | cgtgagcgac | gcatgcatgt | tatgccagac | 1860 |
| gatgatgtgt | tcttcatcac | tgatgtgaaa | atagacgaca | tggggtctca | cagctgcact | 1920 |
| gcccagaact | cggcaggctc | ggtttcagcc | aacgctaccc | tcacagtctt | agaaactcca | 1980 |
| tccttggcag | tgcctctgga | agaccgtgtg | gtaactgtgg | gagaaacagt | ggccttccag | 2040 |

```
tgcaaagcaa ccgggagccc cacaccacgc atcacctggc ttaagggagg tcgcccattg    2100
agcctcacag agcgccacca tttcactcca ggcaaccagc tgctggttgt tcagaatgtg    2160
atgatagacg atgcagggcg gtatacctgt gagatgtcta atcccctggg cactgagcga    2220
gcacatagcc agctgagcat tttacctacc cctggctgcc ggaaggatgg gaccaccgta    2280
ggc                                                                  2283
```

```
<210> SEQ ID NO 5
<211> LENGTH: 5
<212> TYPE: PRT
<213> ORGANISM: Artificial Sequence
<220> FEATURE:
<223> OTHER INFORMATION: A7 heavy chain CDR 1

<400> SEQUENCE: 5

Gly Tyr Asp Met Ser
1               5

<210> SEQ ID NO 6
<211> LENGTH: 9
<212> TYPE: PRT
<213> ORGANISM: Artificial Sequence
<220> FEATURE:
<223> OTHER INFORMATION: A7 heavy chain CDR 2

<400> SEQUENCE: 6

Leu Ile Tyr Pro Asp Ser Gly Asn Lys
1               5

<210> SEQ ID NO 7
<211> LENGTH: 13
<212> TYPE: PRT
<213> ORGANISM: Artificial Sequence
<220> FEATURE:
<223> OTHER INFORMATION: A7 heavy chain CDR 3

<400> SEQUENCE: 7

Arg Asp Ala Gly Leu Ser Trp Ala Gly Ala Phe Asp Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: A7 light chain CDR 1

<400> SEQUENCE: 8

Ser Gly Ser Ser Ser Asn Ile Gly Ser Asn Tyr Val Thr
1               5                   10

<210> SEQ ID NO 9
<211> LENGTH: 4
<212> TYPE: PRT
<213> ORGANISM: Artificial Sequence
<220> FEATURE:
<223> OTHER INFORMATION: A7 light chain CDR 2

<400> SEQUENCE: 9

Ser Asp Ser His
1

<210> SEQ ID NO 10
<211> LENGTH: 9
```

-continued

```
<212> TYPE: PRT
<213> ORGANISM: Artificial Sequence
<220> FEATURE:
<223> OTHER INFORMATION: A7 light chain CDR 3

<400> SEQUENCE: 10

Gly Ser Trp Asp Tyr Ser Leu Ser Ala
1               5

<210> SEQ ID NO 11
<211> LENGTH: 141
<212> TYPE: PRT
<213> ORGANISM: Artificial Sequence
<220> FEATURE:
<223> OTHER INFORMATION: A7 heavy chain_variable region

<400> SEQUENCE: 11

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Gly Tyr Asp Met Ser Trp Val Arg Gln Ala Pro Gly Lys Gly
    50                  55                  60

Leu Glu Trp Val Ser Leu Ile Tyr Pro Asp Ser Gly Asn Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Ala Gly Leu Ser Trp Ala Gly Ala Phe
        115                 120                 125

Asp Tyr Trp Gly Gln Gly Thr Leu Val Thr Val Ser Ser
    130                 135                 140

<210> SEQ ID NO 12
<211> LENGTH: 130
<212> TYPE: PRT
<213> ORGANISM: Artificial Sequence
<220> FEATURE:
<223> OTHER INFORMATION: A7 light chain_variable region

<400> SEQUENCE: 12

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Tyr Val Thr Trp Tyr Gln Gln Leu Pro Gly Thr Ala
    50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Gln Ser Glu Asp Glu Ala Asp Tyr Tyr Cys Gly Ser Trp
            100                 105                 110

Asp Tyr Ser Leu Ser Ala Tyr Val Phe Gly Gly Gly Thr Lys Leu Thr
```

Val Leu
   130

<210> SEQ ID NO 13
<211> LENGTH: 5
<212> TYPE: PRT
<213> ORGANISM: Artificial Sequence
<220> FEATURE:
<223> OTHER INFORMATION: C8 heavy chain CDR 1

<400> SEQUENCE: 13

Asn Tyr Tyr Met Ser
1               5

<210> SEQ ID NO 14
<211> LENGTH: 9
<212> TYPE: PRT
<213> ORGANISM: Artificial Sequence
<220> FEATURE:
<223> OTHER INFORMATION: C8 heavy chain CDR 2

<400> SEQUENCE: 14

Gly Ile Ser Pro Gly Asp Ser Ser Thr
1               5

<210> SEQ ID NO 15
<211> LENGTH: 13
<212> TYPE: PRT
<213> ORGANISM: Artificial Sequence
<220> FEATURE:
<223> OTHER INFORMATION: C8 heavy chain CDR 3

<400> SEQUENCE: 15

Lys Gly Leu Tyr Ser Asn Pro Asn Glu Pro Phe Asp Tyr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: C8 light chain CDR 1

<400> SEQUENCE: 16

Thr Gly Ser Ser Ser Asn Ile Gly Ser Asn Tyr Val Ser
1               5                   10

<210> SEQ ID NO 17
<211> LENGTH: 4
<212> TYPE: PRT
<213> ORGANISM: Artificial Sequence
<220> FEATURE:
<223> OTHER INFORMATION: C8 light chain CDR 2

<400> SEQUENCE: 17

Asp Asp Ser Gln
1

<210> SEQ ID NO 18
<211> LENGTH: 9
<212> TYPE: PRT
<213> ORGANISM: Artificial Sequence
<220> FEATURE:
<223> OTHER INFORMATION: C8 light chain CDR 3

<400> SEQUENCE: 18

```
Gly Thr Trp Asp Tyr Ser Leu Asn Gly
1               5
```

<210> SEQ ID NO 19
<211> LENGTH: 141
<212> TYPE: PRT
<213> ORGANISM: Artificial Sequence
<220> FEATURE:
<223> OTHER INFORMATION: C8 heavy chain_variable region

<400> SEQUENCE: 19

```
Met Glu Thr Asp Thr Leu Leu Leu Trp Val Leu Leu Trp Val Pro
1               5                   10                  15

Gly Ser Thr Trp Glu Val Gln Leu Leu Glu Ser Gly Gly Leu Val
                20                  25                  30

Gln Pro Gly Gly Ser Leu Arg Leu Ser Cys Ala Ala Ser Gly Phe Thr
                35                  40                  45

Phe Ser Asn Tyr Tyr Met Ser Trp Val Arg Gln Ala Pro Gly Lys Gly
    50                  55                  60

Leu Glu Trp Val Ser Gly Ile Ser Pro Gly Asp Ser Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
                100                 105                 110

Val Tyr Tyr Cys Ala Lys Gly Leu Tyr Ser Asn Pro Asn Glu Pro Phe
                115                 120                 125

Asp Tyr Trp Gly Gln Gly Thr Leu Val Thr Val Ser Ser
                130                 135                 140
```

<210> SEQ ID NO 20
<211> LENGTH: 130
<212> TYPE: PRT
<213> ORGANISM: Artificial Sequence
<220> FEATURE:
<223> OTHER INFORMATION: C8 light chain_variable region

<400> SEQUENCE: 20

```
Met Glu Thr Asp Thr Leu Leu Leu Trp Val Leu Leu Trp Val Pro
1               5                   10                  15

Gly Ser Thr Trp Gln Ser Val Leu Thr Gln Pro Pro Ser Ala Ser Gly
                20                  25                  30

Thr Pro Gly Gln Arg Val Thr Ile Ser Cys Thr Gly Ser Ser Ser Asn
                35                  40                  45

Ile Gly Ser Asn Tyr Val Ser Trp Tyr Gln Gln Leu Pro Gly Thr Ala
    50                  55                  60

Pro Lys Leu Leu Ile Tyr Asp Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Thr Trp
                100                 105                 110

Asp Tyr Ser Leu Asn Gly Tyr Val Phe Gly Gly Gly Thr Lys Leu Thr
                115                 120                 125

Val Leu
    130
```

```
<210> SEQ ID NO 21
<211> LENGTH: 5
<212> TYPE: PRT
<213> ORGANISM: Artificial Sequence
<220> FEATURE:
<223> OTHER INFORMATION: E7 heavy chain CDR 1

<400> SEQUENCE: 21

Ser Tyr Asp Met Ser
1               5

<210> SEQ ID NO 22
<211> LENGTH: 9
<212> TYPE: PRT
<213> ORGANISM: Artificial Sequence
<220> FEATURE:
<223> OTHER INFORMATION: E7 heavy chain CDR 2

<400> SEQUENCE: 22

Gly Ile Ser Pro Asp Gly Ser Asn Ile
1               5

<210> SEQ ID NO 23
<211> LENGTH: 19
<212> TYPE: PRT
<213> ORGANISM: Artificial Sequence
<220> FEATURE:
<223> OTHER INFORMATION: E7 heavy chain CDR 3

<400> SEQUENCE: 23

Lys Val Gly Leu Arg Cys Arg Tyr Glu Ala Cys Ser Tyr Ala Tyr Gly
1               5                   10                  15

Met Asp Val

<210> SEQ ID NO 24
<211> LENGTH: 13
<212> TYPE: PRT
<213> ORGANISM: Artificial Sequence
<220> FEATURE:
<223> OTHER INFORMATION: E7 light chain CDR 1

<400> SEQUENCE: 24

Ser Gly Ser Ser Ser Asn Ile Gly Ser Asn Tyr Val Ser
1               5                   10

<210> SEQ ID NO 25
<211> LENGTH: 4
<212> TYPE: PRT
<213> ORGANISM: Artificial Sequence
<220> FEATURE:
<223> OTHER INFORMATION: E7 light chain CDR 2

<400> SEQUENCE: 25

Ser Asp Ser His
1

<210> SEQ ID NO 26
<211> LENGTH: 9
<212> TYPE: PRT
<213> ORGANISM: Artificial Sequence
<220> FEATURE:
<223> OTHER INFORMATION: E7 light chain CDR 3

<400> SEQUENCE: 26

Ala Thr Trp Asp Ser Ser Leu Asn Gly
1               5
```

<210> SEQ ID NO 27
<211> LENGTH: 136
<212> TYPE: PRT
<213> ORGANISM: Artificial Sequence
<220> FEATURE:
<223> OTHER INFORMATION: E7 heavy chain_variable region

<400> SEQUENCE: 27

```
Met Glu Thr Asp Thr Leu Leu Leu Trp Val Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ser Tyr Asp Met Ser Trp Val Arg Gln Ala Pro Gly Lys Gly
    50                  55                  60

Leu Glu Trp Val Ser Gly Ile Ser Pro Asp Gly Ser Asn Ile Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Val Gly Leu Arg Cys Arg Tyr Glu Ala Cys
        115                 120                 125

Ser Tyr Ala Tyr Gly Met Asp Val
    130                 135
```

<210> SEQ ID NO 28
<211> LENGTH: 130
<212> TYPE: PRT
<213> ORGANISM: Artificial Sequence
<220> FEATURE:
<223> OTHER INFORMATION: E7 light chain_variable region

<400> SEQUENCE: 28

```
Met Glu Thr Asp Thr Leu Leu Leu Trp Val Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Tyr Val Ser Trp Tyr Gln Gln Leu Pro Gly Thr Ala
    50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Thr Trp
            100                 105                 110

Asp Ser Ser Leu Asn Gly Tyr Val Phe Gly Gly Gly Thr Lys Leu Thr
        115                 120                 125

Val Leu
    130
```

<210> SEQ ID NO 29
<211> LENGTH: 5
<212> TYPE: PRT
<213> ORGANISM: Artificial Sequence

```
<220> FEATURE:
<223> OTHER INFORMATION: G3 heavy chain CDR 1

<400> SEQUENCE: 29

Asn Tyr Asp Met Ser
1               5

<210> SEQ ID NO 30
<211> LENGTH: 9
<212> TYPE: PRT
<213> ORGANISM: Artificial Sequence
<220> FEATURE:
<223> OTHER INFORMATION: G3 heavy chain CDR 2

<400> SEQUENCE: 30

Ser Ile Ser Pro Ser Ser Gly Ser Ile
1               5

<210> SEQ ID NO 31
<211> LENGTH: 13
<212> TYPE: PRT
<213> ORGANISM: Artificial Sequence
<220> FEATURE:
<223> OTHER INFORMATION: G3 heavy chain CDR 3

<400> SEQUENCE: 31

Lys Asp Leu Asp Ala Phe Trp Arg Pro Ser Phe Asp Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: G3 light chain CDR 1

<400> SEQUENCE: 32

Thr Gly Ser Ser Ser Asn Ile Gly Asn Asn Asn Val Asn
1               5                   10

<210> SEQ ID NO 33
<211> LENGTH: 4
<212> TYPE: PRT
<213> ORGANISM: Artificial Sequence
<220> FEATURE:
<223> OTHER INFORMATION: G3 light chain CDR 2

<400> SEQUENCE: 33

Ser Asp Ser His
1

<210> SEQ ID NO 34
<211> LENGTH: 9
<212> TYPE: PRT
<213> ORGANISM: Artificial Sequence
<220> FEATURE:
<223> OTHER INFORMATION: G3 light chain CDR 3

<400> SEQUENCE: 34

Gly Ser Trp Asp Asp Ser Leu Ser Ala
1               5

<210> SEQ ID NO 35
<211> LENGTH: 141
<212> TYPE: PRT
<213> ORGANISM: Artificial Sequence
<220> FEATURE:
```

<223> OTHER INFORMATION: G3 heavy chain_variable region

<400> SEQUENCE: 35

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Asp Met Ser Trp Val Arg Gln Ala Pro Gly Lys Gly
    50                  55                  60

Leu Glu Trp Val Ser Ser Ile Ser Pro Ser Gly Ser Ile Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Asp Leu Asp Ala Phe Trp Arg Pro Ser Phe
        115                 120                 125

Asp Tyr Trp Gly Gln Gly Thr Leu Val Thr Val Ser Ser
    130                 135                 140

<210> SEQ ID NO 36
<211> LENGTH: 130
<212> TYPE: PRT
<213> ORGANISM: Artificial Sequence
<220> FEATURE:
<223> OTHER INFORMATION: G3 light chain_variable region

<400> SEQUENCE: 36

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Thr Gly Ser Ser Ser Asn
        35                  40                  45

Ile Gly Asn Asn Asn Val Asn Trp Tyr Gln Gln Leu Pro Gly Thr Ala
    50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ser Trp
            100                 105                 110

Asp Asp Ser Leu Ser Ala Tyr Val Phe Gly Gly Gly Thr Lys Leu Thr
        115                 120                 125

Val Leu
    130

<210> SEQ ID NO 37
<211> LENGTH: 328
<212> TYPE: PRT
<213> ORGANISM: Mus musculus

<400> SEQUENCE: 37

Thr Thr Ala Pro Ser Val Tyr Pro Leu Ala Pro Val Cys Gly Asp Thr
1               5                   10                  15

Thr Gly Ser Ser Val Thr Leu Gly Cys Leu Val Lys Gly Tyr Phe Pro
            20                  25                  30

Glu Pro Val Thr Leu Thr Trp Asn Ser Gly Ser Leu Ser Ser Gly Val
            35                  40                  45

His Thr Phe Pro Ala Val Leu Gln Ser Asp Leu Tyr Thr Leu Ser Ser
        50                  55                  60

Ser Val Thr Val Thr Ser Ser Thr Trp Pro Ser Gln Ser Ile Thr Cys
65                  70                  75                  80

Asn Val Ala His Pro Ala Ser Ser Thr Lys Val Asp Lys Lys Ile Glu
                85                  90                  95

Pro Arg Gly Pro Thr Ile Lys Pro Cys Pro Pro Cys Lys Cys Pro Ala
            100                 105                 110

Pro Asn Leu Leu Gly Gly Pro Ser Val Phe Ile Phe Pro Pro Lys Ile
        115                 120                 125

Lys Asp Val Leu Met Ile Ser Leu Ser Pro Ile Val Thr Cys Val Val
130                 135                 140

Val Asp Val Ser Glu Asp Asp Pro Asp Val Gln Ile Ser Trp Phe Val
145                 150                 155                 160

Asn Asn Val Glu Val His Thr Ala Gln Thr Gln Thr His Arg Glu Asp
                165                 170                 175

Tyr Asn Ser Thr Leu Arg Val Val Ser Ala Leu Pro Ile Gln His Gln
            180                 185                 190

Asp Trp Met Ser Gly Lys Glu Phe Lys Cys Lys Val Asn Asn Lys Asp
        195                 200                 205

Leu Pro Ala Pro Ile Glu Arg Thr Ile Ser Lys Pro Lys Gly Ser Val
210                 215                 220

Arg Ala Pro Gln Val Tyr Val Leu Pro Pro Glu Glu Glu Met Thr
225                 230                 235                 240

Lys Lys Gln Val Thr Leu Thr Cys Met Val Thr Asp Phe Met Pro Glu
                245                 250                 255

Asp Ile Tyr Val Glu Trp Thr Asn Asn Gly Lys Thr Glu Leu Asn Tyr
            260                 265                 270

Lys Asn Thr Glu Pro Val Leu Asp Ser Asp Gly Ser Tyr Phe Met Tyr
        275                 280                 285

Ser Lys Leu Arg Val Glu Lys Lys Asn Trp Val Glu Arg Asn Ser Tyr
290                 295                 300

Ser Cys Ser Val Val His Glu Gly Leu His Asn His His Thr Thr Lys
305                 310                 315                 320

Ser Phe Ser Arg Thr Pro Gly Lys
                325

<210> SEQ ID NO 38
<211> LENGTH: 107
<212> TYPE: PRT
<213> ORGANISM: Mus musculus

<400> SEQUENCE: 38

Arg Thr Val Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

```
Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105

<210> SEQ ID NO 39
<211> LENGTH: 330
<212> TYPE: PRT
<213> ORGANISM: Homo sapiens

<400> SEQUENCE: 39

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 40
<211> LENGTH: 107
<212> TYPE: PRT
<213> ORGANISM: Homo sapiens

<400> SEQUENCE: 40

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 41
<211> LENGTH: 326
<212> TYPE: PRT
<213> ORGANISM: Homo sapiens

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu

```
                    210                 215                 220
Pro Gln Val Tyr Thr Leu Pro Ser Arg Glu Glu Met Thr Lys Asn
225                 230                 235                 240

Gln Val Ser Leu Thr Cys Leu Val Lys Gly Phe Tyr Pro Ser Asp Ile
                    245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 42
<211> LENGTH: 377
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 43
<211> LENGTH: 327
<212> TYPE: PRT
<213> ORGANISM: Homo sapiens

<400> SEQUENCE: 43

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

-continued

Ile Ala Val Glu Trp Glu Ser Asn Gly Gln Pro Glu Asn Asn Tyr Lys
              260                 265                 270

Thr Thr Pro Pro Val Leu Asp Ser Asp Gly Ser Phe Phe Leu Tyr Ser
              275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 44
<211> LENGTH: 245
<212> TYPE: PRT
<213> ORGANISM: Artificial Sequence
<220> FEATURE:
<223> OTHER INFORMATION: Hybrid Fc_Heavy region

<400> SEQUENCE: 44

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
              20                  25                  30

Thr Gln Pro Leu Gly Val Phe Leu Phe Pro Pro Lys Pro Lys Asp Thr
          35                  40                  45

Leu Met Ile Ser Arg Thr Pro Glu Val Thr Cys Val Val Val Asp Val
      50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                  85                  90                  95

Thr Tyr Arg Val Val Ser Val Leu Thr Val Leu His Gln Asp Trp Leu
              100                 105                 110

Asn Gly Lys Glu Tyr Lys Cys Lys Val Ser Asn Lys Gly Leu Pro Ser
          115                 120                 125

Ser Ile Glu Lys Thr Ile Ser Lys Ala Lys Gly Gln Pro Arg Glu Pro
      130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                  165                 170                 175

Val Glu Trp Glu Ser Asn Gly Gln Pro Glu Asn Asn Tyr Lys Thr Thr
              180                 185                 190

Pro Pro Val Leu Asp Ser Asp Gly Ser Phe Phe Leu Tyr Ser Arg Leu
          195                 200                 205

Thr Val Asp Lys Ser Arg Trp Gln Glu Gly Asn Val Phe Ser Cys Ser
      210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 45
<211> LENGTH: 469
<212> TYPE: PRT
<213> ORGANISM: Artificial Sequence
<220> FEATURE:
<223> OTHER INFORMATION: A7 heavy chain_mouse IgG2 Fc_full sequence

<400> SEQUENCE: 45

```
Met Glu Thr Asp Thr Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Gly Tyr Asp Met Ser Trp Val Arg Gln Ala Pro Gly Lys Gly
    50                  55                  60

Leu Glu Trp Val Ser Leu Ile Tyr Pro Asp Ser Gly Asn Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Ala Gly Leu Ser Trp Ala Gly Ala Phe
        115                 120                 125

Asp Tyr Trp Gly Gln Gly Thr Leu Val Thr Val Ser Ser Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
    210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
    290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
            340                 345                 350

Pro Ile Glu Arg Thr Ile Ser Lys Pro Lys Gly Ser Val Arg Ala Pro
        355                 360                 365

Gln Val Tyr Val Leu Pro Pro Pro Glu Glu Glu Met Thr Lys Lys Gln
    370                 375                 380

Val Thr Leu Thr Cys Met Val Thr Asp Phe Met Pro Glu Asp Ile Tyr
385                 390                 395                 400
```

Val Glu Trp Thr Asn Asn Gly Lys Thr Glu Leu Asn Tyr Lys Asn Thr
            405                 410                 415

Glu Pro Val Leu Asp Ser Asp Gly Ser Tyr Phe Met Tyr Ser Lys Leu
        420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
    450                 455                 460

Arg Thr Pro Gly Lys
465

<210> SEQ ID NO 46
<211> LENGTH: 237
<212> TYPE: PRT
<213> ORGANISM: Artificial Sequence
<220> FEATURE:
<223> OTHER INFORMATION: A7 light chain_mouse IgG2 Fc_full sequence

<400> SEQUENCE: 46

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Tyr Val Thr Trp Tyr Gln Gln Leu Pro Gly Thr Ala
    50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Gln Ser Glu Asp Glu Ala Asp Tyr Tyr Cys Gly Ser Trp
            100                 105                 110

Asp Tyr Ser Leu Ser Ala Tyr Val Phe Gly Gly Gly Thr Lys Leu Thr
        115                 120                 125

Val Leu Arg Thr Val Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 47
<211> LENGTH: 469
<212> TYPE: PRT
<213> ORGANISM: Artificial Sequence
<220> FEATURE:
<223> OTHER INFORMATION: C8 heavy chain_mouse IgG2 Fc_full sequence -continued

```
<400> SEQUENCE: 47

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Tyr Met Ser Trp Val Arg Gln Ala Pro Gly Lys Gly
    50                  55                  60

Leu Glu Trp Val Ser Gly Ile Ser Pro Gly Asp Ser Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Gly Leu Tyr Ser Asn Pro Asn Glu Pro Phe
        115                 120                 125

Asp Tyr Trp Gly Gln Gly Thr Leu Val Thr Val Ser Ser Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
    290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
            340                 345                 350

Pro Ile Glu Arg Thr Ile Ser Lys Pro Lys Gly Ser Val Arg Ala Pro
        355                 360                 365

Gln Val Tyr Val Leu Pro Pro Pro Glu Glu Met Thr Lys Lys Gln
    370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415
```

```
Glu Pro Val Leu Asp Ser Asp Gly Ser Tyr Phe Met Tyr Ser Lys Leu
            420                 425                 430
Arg Val Glu Lys Lys Asn Trp Val Glu Arg Asn Ser Tyr Ser Cys Ser
            435                 440                 445
Val Val His Glu Gly Leu His Asn His His Thr Thr Lys Ser Phe Ser
            450                 455                 460
Arg Thr Pro Gly Lys
465

<210> SEQ ID NO 48
<211> LENGTH: 237
<212> TYPE: PRT
<213> ORGANISM: Artificial Sequence
<220> FEATURE:
<223> OTHER INFORMATION: C8 light chain_mouse IgG2 Fc_full sequence

<400> SEQUENCE: 48

Met Glu Thr Asp Thr Leu Leu Trp Val Leu Leu Trp Val Pro
1               5                   10                  15
Gly Ser Thr Trp Gln Ser Val Leu Thr Gln Pro Pro Ser Ala Ser Gly
            20                  25                  30
Thr Pro Gly Gln Arg Val Thr Ile Ser Cys Thr Gly Ser Ser Ser Asn
            35                  40                  45
Ile Gly Ser Asn Tyr Val Ser Trp Tyr Gln Gln Leu Pro Gly Thr Ala
        50                  55                  60
Pro Lys Leu Leu Ile Tyr Asp Asp Ser Gln Arg Pro Ser Gly Val Pro
65                  70                  75                  80
Asp Arg Phe Ser Gly Ser Lys Ser Gly Thr Ser Ala Ser Leu Ala Ile
                85                  90                  95
Ser Gly Leu Arg Ser Glu Asp Glu Ala Asp Tyr Tyr Cys Gly Thr Trp
            100                 105                 110
Asp Tyr Ser Leu Asn Gly Tyr Val Phe Gly Gly Gly Thr Lys Leu Thr
            115                 120                 125
Val Leu Arg Thr Val Ala Ala Pro Thr Val Ser Ile Phe Pro Pro Ser
    130                 135                 140
Ser Glu Gln Leu Thr Ser Gly Gly Ala Ser Val Val Cys Phe Leu Asn
145                 150                 155                 160
Asn Phe Tyr Pro Lys Asp Ile Asn Val Lys Trp Lys Ile Asp Gly Ser
                165                 170                 175
Glu Arg Gln Asn Gly Val Leu Asn Ser Trp Thr Asp Gln Asp Ser Lys
            180                 185                 190
Asp Ser Thr Tyr Ser Met Ser Ser Thr Leu Thr Leu Thr Lys Asp Glu
            195                 200                 205
Tyr Glu Arg His Asn Ser Tyr Thr Cys Glu Ala Thr His Lys Thr Ser
    210                 215                 220
Thr Ser Pro Ile Val Lys Ser Phe Asn Arg Asn Glu Cys
225                 230                 235

<210> SEQ ID NO 49
<211> LENGTH: 475
<212> TYPE: PRT
<213> ORGANISM: Artificial Sequence
<220> FEATURE:
<223> OTHER INFORMATION: E7 heavy chain_mouse IgG2 Fc_full sequence

<400> SEQUENCE: 49

Met Glu Thr Asp Thr Leu Leu Leu Trp Val Leu Leu Leu Trp Val Pro
```

-continued

```
1               5                   10                  15
Gly Ser Thr Trp Glu Val Gln Leu Leu Glu Ser Gly Gly Gly Leu Val
                20                  25                  30
Gln Pro Gly Gly Ser Leu Arg Leu Ser Cys Ala Ala Ser Gly Phe Thr
                35                  40                  45
Phe Ser Ser Tyr Asp Met Ser Trp Val Arg Gln Ala Pro Gly Lys Gly
                50                  55                  60
Leu Glu Trp Val Ser Gly Ile Ser Pro Asp Gly Ser Asn Ile Tyr Tyr
65                  70                  75                  80
Ala Asp Ser Val Lys Gly Arg Phe Thr Ile Ser Arg Asp Asn Ser Lys
                85                  90                  95
Asn Thr Leu Tyr Leu Gln Met Asn Ser Leu Arg Ala Glu Asp Thr Ala
                100                 105                 110
Val Tyr Tyr Cys Ala Lys Val Gly Leu Arg Cys Arg Tyr Glu Ala Cys
                115                 120                 125
Ser Tyr Ala Tyr Gly Met Asp Val Trp Gly Gln Gly Thr Leu Val Thr
                130                 135                 140
Val Ser Ser Thr Thr Ala Pro Ser Val Tyr Pro Leu Ala Pro Val Cys
145                 150                 155                 160
Gly Asp Thr Thr Gly Ser Ser Val Thr Leu Gly Cys Leu Val Lys Gly
                165                 170                 175
Tyr Phe Pro Glu Pro Val Thr Leu Thr Trp Asn Ser Gly Ser Leu Ser
                180                 185                 190
Ser Gly Val His Thr Phe Pro Ala Val Leu Gln Ser Asp Leu Tyr Thr
                195                 200                 205
Leu Ser Ser Ser Val Thr Val Thr Ser Ser Thr Trp Pro Ser Gln Ser
210                 215                 220
Ile Thr Cys Asn Val Ala His Pro Ala Ser Ser Thr Lys Val Asp Lys
225                 230                 235                 240
Lys Ile Glu Pro Arg Gly Pro Thr Ile Lys Pro Cys Pro Pro Cys Lys
                245                 250                 255
Cys Pro Ala Pro Asn Leu Leu Gly Gly Pro Ser Val Phe Ile Phe Pro
                260                 265                 270
Pro Lys Ile Lys Asp Val Leu Met Ile Ser Leu Ser Pro Ile Val Thr
                275                 280                 285
Cys Val Val Val Asp Val Ser Glu Asp Pro Asp Val Gln Ile Ser
                290                 295                 300
Trp Phe Val Asn Asn Val Glu Val His Thr Ala Gln Thr Gln Thr His
305                 310                 315                 320
Arg Glu Asp Tyr Asn Ser Thr Leu Arg Val Val Ser Ala Leu Pro Ile
                325                 330                 335
Gln His Gln Asp Trp Met Ser Gly Lys Glu Phe Lys Cys Lys Val Asn
                340                 345                 350
Asn Lys Asp Leu Pro Ala Pro Ile Glu Arg Thr Ile Ser Lys Pro Lys
                355                 360                 365
Gly Ser Val Arg Ala Pro Gln Val Tyr Val Leu Pro Pro Glu Glu
                370                 375                 380
Glu Met Thr Lys Lys Gln Val Thr Leu Thr Cys Met Val Thr Asp Phe
385                 390                 395                 400
Met Pro Glu Asp Ile Tyr Val Glu Trp Thr Asn Asn Gly Lys Thr Glu
                405                 410                 415
Leu Asn Tyr Lys Asn Thr Glu Pro Val Leu Asp Ser Asp Gly Ser Tyr
                420                 425                 430
```

```
Phe Met Tyr Ser Lys Leu Arg Val Glu Lys Asn Trp Val Glu Arg
        435                 440                 445

Asn Ser Tyr Ser Cys Ser Val Val His Glu Gly Leu His Asn His His
        450                 455                 460

Thr Thr Lys Ser Phe Ser Arg Thr Pro Gly Lys
465                 470                 475

<210> SEQ ID NO 50
<211> LENGTH: 237
<212> TYPE: PRT
<213> ORGANISM: Artificial Sequence
<220> FEATURE:
<223> OTHER INFORMATION: E7 light chain_mouse IgG2 Fc_full sequence

<400> SEQUENCE: 50

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Tyr Val Ser Trp Tyr Gln Gln Leu Pro Gly Thr Ala
    50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Thr Trp
            100                 105                 110

Asp Ser Ser Leu Asn Gly Tyr Val Phe Gly Gly Gly Thr Lys Leu Thr
        115                 120                 125

Val Leu Arg Thr Val Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 51
<211> LENGTH: 469
<212> TYPE: PRT
<213> ORGANISM: Artificial Sequence
<220> FEATURE:
<223> OTHER INFORMATION: G3 heavy chain_mouse IgG2 Fc_full sequence

<400> SEQUENCE: 51

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
```

```
                   20                  25                  30
    Gln Pro Gly Gly Ser Leu Arg Leu Ser Cys Ala Ala Ser Gly Phe Thr
                    35                  40                  45
    Phe Ser Asn Tyr Asp Met Ser Trp Val Arg Gln Ala Pro Gly Lys Gly
                    50                  55                  60
    Leu Glu Trp Val Ser Ser Ile Ser Pro Ser Gly Ser Ile Tyr Tyr
    65                  70                  75                  80
    Ala Asp Ser Val Lys Gly Arg Phe Thr Ile Ser Arg Asp Asn Ser Lys
                    85                  90                  95
    Asn Thr Leu Tyr Leu Gln Met Asn Ser Leu Arg Ala Glu Asp Thr Ala
                    100                 105                 110
    Val Tyr Tyr Cys Ala Lys Asp Leu Asp Ala Phe Trp Arg Pro Ser Phe
                    115                 120                 125
    Asp Tyr Trp Gly Gln Gly Thr Leu Val Thr Val Ser Ser Thr Thr Ala
                    130                 135                 140
    Pro Ser Val Tyr Pro Leu Ala Pro Val Cys Gly Asp Thr Thr Gly Ser
    145                 150                 155                 160
    Ser Val Thr Leu Gly Cys Leu Val Lys Gly Tyr Phe Pro Glu Pro Val
                    165                 170                 175
    Thr Leu Thr Trp Asn Ser Gly Ser Leu Ser Ser Gly Val His Thr Phe
                    180                 185                 190
    Pro Ala Val Leu Gln Ser Asp Leu Tyr Thr Leu Ser Ser Ser Val Thr
                    195                 200                 205
    Val Thr Ser Ser Thr Trp Pro Ser Gln Ser Ile Thr Cys Asn Val Ala
                    210                 215                 220
    His Pro Ala Ser Ser Thr Lys Val Asp Lys Lys Ile Glu Pro Arg Gly
    225                 230                 235                 240
    Pro Thr Ile Lys Pro Cys Pro Pro Cys Lys Cys Pro Ala Pro Asn Leu
                    245                 250                 255
    Leu Gly Gly Pro Ser Val Phe Ile Phe Pro Pro Lys Ile Lys Asp Val
                    260                 265                 270
    Leu Met Ile Ser Leu Ser Pro Ile Val Thr Cys Val Val Val Asp Val
                    275                 280                 285
    Ser Glu Asp Asp Pro Asp Val Gln Ile Ser Trp Phe Val Asn Asn Val
                    290                 295                 300
    Glu Val His Thr Ala Gln Thr Gln Thr His Arg Glu Asp Tyr Asn Ser
    305                 310                 315                 320
    Thr Leu Arg Val Val Ser Ala Leu Pro Ile Gln His Gln Asp Trp Met
                    325                 330                 335
    Ser Gly Lys Glu Phe Lys Cys Lys Val Asn Asn Lys Asp Leu Pro Ala
                    340                 345                 350
    Pro Ile Glu Arg Thr Ile Ser Lys Pro Lys Gly Ser Val Arg Ala Pro
                    355                 360                 365
    Gln Val Tyr Val Leu Pro Pro Pro Glu Glu Glu Met Thr Lys Lys Gln
                    370                 375                 380
    Val Thr Leu Thr Cys Met Val Thr Asp Phe Met Pro Glu Asp Ile Tyr
    385                 390                 395                 400
    Val Glu Trp Thr Asn Asn Gly Lys Thr Glu Leu Asn Tyr Lys Asn Thr
                    405                 410                 415
    Glu Pro Val Leu Asp Ser Asp Gly Ser Tyr Phe Met Tyr Ser Lys Leu
                    420                 425                 430
    Arg Val Glu Lys Lys Asn Trp Val Glu Arg Asn Ser Tyr Ser Cys Ser
                    435                 440                 445
```

```
Val Val His Glu Gly Leu His Asn His His Thr Lys Ser Phe Ser
    450                 455                 460

Arg Thr Pro Gly Lys
465

<210> SEQ ID NO 52
<211> LENGTH: 237
<212> TYPE: PRT
<213> ORGANISM: Artificial Sequence
<220> FEATURE:
<223> OTHER INFORMATION: G3 light chain_mouse IgG2 Fc_full sequence

<400> SEQUENCE: 52

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
                20                  25                  30

Thr Pro Gly Gln Arg Val Thr Ile Ser Cys Thr Gly Ser Ser Ser Asn
            35                  40                  45

Ile Gly Asn Asn Val Asn Trp Tyr Gln Gln Leu Pro Gly Thr Ala
    50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ser Trp
            100                 105                 110

Asp Asp Ser Leu Ser Ala Tyr Val Phe Gly Gly Gly Thr Lys Leu Thr
        115                 120                 125

Val Leu Arg Thr Val Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235
```

UNITED STATES PATENT AND TRADEMARK OFFICE
CERTIFICATE OF CORRECTION

| | | |
|---|---|---|
| PATENT NO. | : 11,279,756 B2 | Page 1 of 1 |
| APPLICATION NO. | : 16/606220 | |
| DATED | : March 22, 2022 | |
| INVENTOR(S) | : Jung Ho Kim et al. | |

It is certified that error appears in the above-identified patent and that said Letters Patent is hereby corrected as shown below:

In the Claims

At Column 84, Line 31, "resection" should be -- rejection --.

Signed and Sealed this
Nineteenth Day of November, 2024

*Katherine Kelly Vidal*

Katherine Kelly Vidal
*Director of the United States Patent and Trademark Office*